US010294491B2

(12) United States Patent
Payne et al.

(10) Patent No.: US 10,294,491 B2
(45) Date of Patent: May 21, 2019

(54) EXPRESSION VECTORS COMPRISING CHIMERIC CYTOMEGALOVIRUS PROMOTER AND ENHANCER SEQUENCES

(71) Applicant: Lonza Biologics PLC., Berkshire (GB)

(72) Inventors: Tom Payne, Cambridge (GB); Robert Young, London (GB); Marc Feary, Suffolk (GB)

(73) Assignee: LONZA BIOLOGICS PLC., Berkshire (GB)

( * ) Notice: Subject to any disclaimer, the term of this patent is extended or adjusted under 35 U.S.C. 154(b) by 78 days.

(21) Appl. No.: 15/687,835

(22) Filed: Aug. 28, 2017

(65) Prior Publication Data

US 2017/0356007 A1 Dec. 14, 2017

Related U.S. Application Data

(62) Division of application No. 14/426,329, filed as application No. PCT/EP2013/069715 on Sep. 23, 2013, now Pat. No. 9,777,290.

(30) Foreign Application Priority Data

Sep. 24, 2012 (EP) ..................................... 12185728

(51) Int. Cl.
*C12N 15/85* (2006.01)
(52) U.S. Cl.
CPC .... *C12N 15/85* (2013.01); *C12N 2710/16122* (2013.01); *C12N 2830/15* (2013.01); *C12N 2830/60* (2013.01)
(58) Field of Classification Search
None
See application file for complete search history.

(56) References Cited

U.S. PATENT DOCUMENTS

2003/0157641 A1  8/2003  Reff
2012/0100573 A1  4/2012  Thudium et al.

FOREIGN PATENT DOCUMENTS

| CN | 1934260 | 3/2007 |
| CN | 102392047 | 3/2012 |
| EP | 0 314 161 | 5/1989 |
| JP | 2006-520589 | 9/2006 |
| JP | 2008-536506 | 9/2008 |
| JP | 6162246 B2 | 7/2017 |
| KR | 10-1757083 B1 | 7/2017 |
| WO | 99/61472 | 12/1999 |
| WO | 02/00897 | 1/2002 |
| WO | 2004/081167 | 9/2004 |
| WO | 2005/035771 | 4/2005 |
| WO | 2006/111387 | 10/2006 |
| WO | 2008/153733 | 12/2008 |

OTHER PUBLICATIONS

Isomura, et al. (2004) "Role of the Proximal Enhancer of the Major Immediate Early Promoter in Human Cytomegalovirus Replication", Journal of Virology, 78(23): 12788-99. (Year: 2004).*
Chang, Y.N. et al., "Simian cytomegalovirus major immediate early transcription unit IE94," GenBank U38308.1, May 5, 2000.
Australian Office Action for Australian Application No. 2013320157, dated Jun. 30, 2016.
Canadian Office Action for Canadian Application No. 2,880,750, dated Mar. 7, 2016.
Canadian Office Action for corresponding Canadian Application No. 2,880,750, dated May 3, 2017.
Chinese Office Action for Chinese Application No. 201380049575. 6, dated Apr. 18, 2016.
Database Geneseq [Online] Feb. 19, 2009, "NTC7382 promoter DNA sequence, SEQ ID 6." retrieved from EBI accession No. GSN:AUR46517. Database accession No. AUR46517.
Eurasian Office Action for corresponding Eurasian Application No. 201590264, dated Feb. 2, 2017.
European Office Action for corresponding European Application No. 13 773 651.8, dated Feb. 23, 2017.

(Continued)

*Primary Examiner* — Robert M Kelly
(74) *Attorney, Agent, or Firm* — Morgan, Lewis & Bockius LLP

(57) ABSTRACT

The present invention relates to expression vectors for the heterologous expression of a nucleic acid sequence of interest in mammalian cells, the vectors comprising a chimeric promoter regulatory sequence being operably linked to a nucleic acid sequence to be expressed, wherein the chimeric promoter regulatory sequence comprises a cytomegalovirus promoter sequence derived from murine cytomegalovirus or from human cytomegalovirus and being operably linked to the transcriptional start site of the nucleic acid sequence to be expressed; and a cytomegalovirus upstream region and/or enhancer sequence derived from human and/or the simian cytomegalovirus, wherein the upstream region and/or enhancer sequence is located 5' of and operably linked to the murine or the human promoter sequence, and wherein the chimeric promoter regulatory sequence comprises sequence elements being derived from at least two of the group consisting of murine cytomegalovirus, human cytomegalovirus and simian cytomegalovirus. In particular embodiments, the chimeric promoter regulatory sequence comprises sequence elements derived from the murine or the human cytomegalovirus IE1 promoter and from the human and/or the simian cytomegalovirus IE1 region. The invention also relates to mammalian host cells transfected with such expression vectors, a method for heterologous expression of a nucleic acid sequence in a mammalian host cell by employing such expression vectors, and the use of such expression vectors for the heterologous expression of a nucleic acid sequence.

14 Claims, 5 Drawing Sheets

Specification includes a Sequence Listing.

(56) References Cited

OTHER PUBLICATIONS

Gustems et al., "In Vivo Competence of Murine Cytomegalovirus Under the Control of the Human Cytomegalovirus Major Immediate-Early Enhancer in the Establishment of Latency and Reactivation," Journal of Virology, Oct. 2008, p. 10302-10307, vol. 82, No. 20.
Hiroki and Stinski (2003) "The Human Cytomegalovirus Major Immediate-Early Enhancer Determines the Efficiency of Immediate-Early Gene Transcription and Viral Replication in Permissive Cells at Low Multiplicity of Infection," Journal of Virology, 77(6): 3602-14.
Japanese Office Action for Japanese Application No. 2015-532436, dated Feb. 15, 2016.
Japanese Notice of Allowance for corresponding Japanese Application No. 2015-532436, dated May 17, 2017.
Keil, G.M. et al., "Novel vectors for simultaneous high-level dual protein expression in vertebrate and insect cells by recombinant baculoviruses," J. Virol. Methods (2009), doi: 10.1016/j.jviromet.2009.05.001.
Korean Notice of Allowance for corresponding Korean Application No. 10-2015-7006996, dated Apr. 26, 2017.
Meier et al., "Regulation of Human Cytomegalovirus Immediate-Early Gene Expression," Intervirology 1996; 39:331-342.
"search result 3," run by the STIC research facilities at the USPTO, no author, no journal, no volume, 2016, 3 pages.
Office Action in corresponding Chinese Application No. 201380049575.6, dated Jun. 27, 2017.
Office Action in corresponding European Application No. 13 773 651.8, dated Sep. 15, 2017.

\* cited by examiner

SEQUENCE LISTING

```
<160> NUMBER OF SEQ ID NOS: 15

<210> SEQ ID NO 1
<211> LENGTH: 5908
<212> TYPE: DNA
<213> ORGANISM: artificial sequence
<220> FEATURE:
<223> OTHER INFORMATION: plasmid vector pRY42
<220> FEATURE:
<221> NAME/KEY: polyA_signal
<222> LOCATION: (7)..(245)
<223> OTHER INFORMATION: SV40 polyA signal
<220> FEATURE:
<221> NAME/KEY: promoter
<222> LOCATION: (266)..(756)
<223> OTHER INFORMATION: mCMV-MIE (IE1) promoter fragment
<220> FEATURE:
<221> NAME/KEY: 5'UTR
```

```
<222> LOCATION: (758)..(791)
<223> OTHER INFORMATION: part of mCMV-MIE (IE1) 5'UTR exon 1
<220> FEATURE:
<221> NAME/KEY: 5'UTR
<222> LOCATION: (803)..(884)
<223> OTHER INFORMATION: part of hCMV-MIE (IE1) 5'UTR exon 1
<220> FEATURE:
<221> NAME/KEY: Intron
<222> LOCATION: (885)..(1711)
<223> OTHER INFORMATION: hCMV-MIE (IE1) intron A
<220> FEATURE:
<221> NAME/KEY: 5'UTR
<222> LOCATION: (1712)..(1729)
<223> OTHER INFORMATION: hCMV-MIE (IE1) 5'UTR exon 2
<220> FEATURE:
<221> NAME/KEY: polyA_signal
<222> LOCATION: (1767)..(2005)
<223> OTHER INFORMATION: SV40 polyA signal
<220> FEATURE:
<221> NAME/KEY: promoter
<222> LOCATION: (2019)..(2345)
<223> OTHER INFORMATION: SV40 early promoter, derived from pFRT/lacZeo
      (Invitrogen)
<220> FEATURE:
<221> NAME/KEY: source
<222> LOCATION: (2350)..(2354)
<223> OTHER INFORMATION: sequence containing ATG site found upstream of
      wild-type FRT in pFRT/lacZeo (Invitrogen)
<220> FEATURE:
<221> NAME/KEY: misc_recomb
<222> LOCATION: (2355)..(2402)
<223> OTHER INFORMATION: wild-type flippase recognition target (FRT)
      site, derived from pcDNA5-Frt (Invitrogen)
<220> FEATURE:
<221> NAME/KEY: source
<222> LOCATION: (3183)..(4043)
<223> OTHER INFORMATION: reverse complement CDS of beta-lactamase gene
<220> FEATURE:
<221> NAME/KEY: misc_recomb
<222> LOCATION: (4319)..(4366)
<223> OTHER INFORMATION: mutant flippase recognition target (FRT) site
<220> FEATURE:
<221> NAME/KEY: promoter
<222> LOCATION: (4410)..(4900)
<223> OTHER INFORMATION: mCMV-MIE (IE1) promoter fragment
<220> FEATURE:
<221> NAME/KEY: 5'UTR
<222> LOCATION: (4902)..(4935)
<223> OTHER INFORMATION: part of mCMV-MIE (IE1) 5'UTR exon 1
<220> FEATURE:
<221> NAME/KEY: 5'UTR
<222> LOCATION: (4947)..(5028)
<223> OTHER INFORMATION: part of hCMV-MIE (IE1) 5'UTR exon 1
<220> FEATURE:
<221> NAME/KEY: Intron
<222> LOCATION: (5029)..(5855)
<223> OTHER INFORMATION: hCMV-MIE (IE1) intron A
<220> FEATURE:
<221> NAME/KEY: 5'UTR
<222> LOCATION: (5856)..(5873)
<223> OTHER INFORMATION: hCMV-MIE (IE1)5'UTR exon 2

<400> SEQUENCE: 1
gaattcattg atcataatca gccataccac atttgtagag gttttacttg ctttaaaaaa      60
cctcccacac ctcccctga acctgaaaca taaaatgaat gcaattgttg ttgttaactt     120
gtttattgca gcttataatg gttacaaata aagcaatagc atcacaaatt tcacaaataa     180
agcatttttt tcactgcatt ctagttgtgg tttgtccaaa ctcatcaatg tatcttatca     240
tgtctggcgg ccgctgaggc gcgcctactg agtcattagg gactttccaa tgggttttgc     300
ccagtacata aggtcaatag gggtgaatca acaggaaagt cccattggag ccaagtacac     360
tgagtcaata gggactttcc attgggtttt gcccagtaca aaaggtcaat agggggtgag     420
tcaatgggtt tttcccatta ttggcacgta cataaggtca ataggggtga gtcattgggt     480
```

```
ttttccagcc aatttaatta aaacgccatg tactttccca ccattgacgt caatgggcta    540
ttgaaactaa tgcaacgtga cctttaaacg gtactttccc atagctgatt aatgggaaag    600
taccgttctc gagccaatac acgtcaatgg gaagtgaaag gcagccaaa acgtaacacc     660 gccccggttt tccctggaa attccatatt ggcacgcatt ctattggctg agctgcgttc     720
tacgtgggta taagaggcgc gaccagcgtc ggtaccgtcg cagtcttcgg tctgaccacc    780
gtagaacgca gcctcaggac ctccatagaa gacaccggga ccgatccagc ctccgcggcc    840
gggaacggtg cattggaacg cggattcccc gtgccaagag tgacgtaagt accgcctata    900
gagtctatag gccaccccc ttggcttctt atgcatgcta tactgttttt ggcttggggt      960
ctatacaccc ccgcttcctc atgttatagg tgatggtata gcttagccta taggtgtggg   1020
ttattgacca ttattgacca ctcccctatt ggtgacgata ctttccatta ctaatccata   1080
acatggctct tgccacaac tctctttatt ggctatatgc caatacactg tccttcagag     1140
actgacacgg actctgtatt tttacaggat ggggtctcat ttattattta caaattcaca   1200
tatacaacac caccgtcccc agtgcccgca gttttatta aacataacgt gggatctcca    1260
cgcgaatctc gggtacgtgt tccggacatg ggctcttctc cggtagcggc ggagcttcta   1320
catccgagcc ctgctcccat gcctccagcg actcatggtc gctcggcagc tccttgctcc   1380
taacagtgga ggccagactt aggcacagca cgatgcccac caccaccagt gtgccgcaca   1440
aggccgtggc ggtagggtat gtgtctgaaa atgagctcgg ggagcgggct tgcaccgctg   1500
acgcatttgg aagacttaag gcagcggcag aagaagatgc aggcagctga gttgttgtgt   1560
tctgataaga gtcagaggta actcccgttg cggtgctgtt aacggtggag ggcagtgtag   1620
tctgagcagt actcgttgct gccgcgcgcg ccaccagaca taatagctga cagactaaca   1680
gactgttcct ttccatgggt ctttctgca gtcaccgtcc ttgacacggg atccggcgcg    1740
cccctagggg taccgtcgac tcgcgaattg atcataatca gccataccac atttgtagag   1800
gttttacttg cttaaaaaa cctcccacac ctcccctga acctgaaaca taaaatgaat     1860
gcaattgttg ttgttaactt gtttattgca gcttataatg gttacaaata aagcaatagc   1920
atcacaaatt tcacaaataa agcattttt tcactgcatt ctagttgtgg tttgtccaaa    1980
ctcatcaatg tatcttatca tgtctggatc agcttgagca gctgtggaat gtgtgtcagt   2040
tagggtgtgg aaagtcccca ggctcccag caggcagaag tatgcaaagc atgcatctca    2100
attagtcagc aaccaggtgt ggaaagtccc caggctcccc agcaggcaga agtatgcaaa   2160
gcatgcatct caattagtca gcaaccatag tcccgcccct aactccgccc atccgcccc    2220 taactccgcc cagttccgcc cattctccgc cccatggctg actaattttt tttatttatg   2280
cagaggccga ggccgcctcg gcctctgagc tattccagaa gtagtgagga ggcttttttg   2340
gaggctacca tggagaagtt actattccga agttcctatt ctctagaaag tataggaact   2400
tctcgggccg cgttgctggc gttttttccat aggctccgcc cccctgacga gcatcacaaa   2460
aatcgacgct caagtcagag gtggcgaaac ccgacaggac tataaagata ccaggcgttt   2520
ccccctggaa gctccctcgt gcgctctcct gttccgaccc tgccgcttac cggatacctg   2580 tccgccttc tcccttcggg aagcgtggcg ctttctcata gctcacgctg taggtatctc    2640
agttcggtgt aggtcgttcg ctccaagctg ggctgtgtgc acgaaccccc cgttcagccc   2700
gaccgctgcg ccttatccgg taactatcgt cttgagtcca acccggtaag acacgactta   2760
tcgccactgg cagcagccac tggtaacagg attagcagag cgaggtatgt aggcggtgct   2820
```

```
acagagttct tgaagtggtg gcctaactac ggctacacta gaagaacagt atttggtatc    2880
tgcgctctgc tgaagccagt taccttcgga aaaagagttg gtagctcttg atccggcaaa    2940
caaaccaccg ctggtagcgg tggttttttt gtttgcaagc agcagattac gcgcagaaaa    3000
aaaggatctc aagaagatcc tttgatcttt tctacggggt ctgacgctca gtggaacgaa    3060
aactcacgtt aagggatttt ggtcatgaga ttatcaaaaa ggatcttcac ctagatcctt    3120
ttaaattaaa aatgaagttt taaatcaatc taaagtatat atgagtaaac ttggtctgac    3180
agttaccaat gcttaatcag tgaggcacct atctcagcga tctgtctatt tcgttcatcc    3240
atagttgcct gactccccgt cgtgtagata actacgatac gggagggctt accatctggc    3300
cccagtgctg caatgatacc gcgagaccca cgctcaccgg ctccagattt atcagcaata    3360
aaccagccag ccggaagggc cgagcgcaga agtggtcctg caactttatc cgcctccatc    3420
cagtctatta attgttgccg ggaagctaga gtaagtagtt cgccagttaa tagtttgcgc    3480
aacgttgttg ccattgctac aggcatcgtg gtgtcacgct cgtcgtttgg tatggcttca    3540
ttcagctccg gttcccaacg atcaaggcga gttacatgat cccccatgtt gtgcaaaaaa    3600
gcggttagct ccttcggtcc tccgatcgtt gtcagaagta agttggccgc agtgttatca    3660
ctcatggtta tggcagcact gcataattct cttactgtca tgccatccgt aagatgcttt    3720
tctgtgactg gtgagtactc aaccaagtca ttctgagaat agtgtatgcg gcgaccgagt    3780
tgctcttgcc cggcgtcaat acgggataat accgcgccac atagcagaac tttaaaagtg    3840
ctcatcattg gaaaacgttc ttcggggcga aaactctcaa ggatcttacc gctgttgaga    3900
tccagttcga tgtaacccac tcgtgcaccc aactgatctt cagcatcttt tactttcacc    3960
agcgtttctg ggtgagcaaa aacaggaagg caaaatgccg caaaaaaggg aataagggcg    4020
acacggaaat gttgaatact catactcttc ctttttcaat attattgaag catttatcag    4080
ggttattgtc tcatgagcgg atacatattt gaatgtattt agaaaaataa acaaatagggg   4140 gttccgcgca catttccccg aaaagtgcca cctgacgtct aagaaaccat tattatcatg    4200
acattaacct ataaaaatag gcgtatcacg aggccctgat ggctctttgc ggcacccatc    4260
gttcgtaatg ttccgtggca ccgaggacaa ccctcaagag aaaatgtaat cacactggga    4320
agttcctatt ccgaagttcc tattcttcaa aaggtatagg aacttcctgc agtgaataat    4380
aaaatgtgtg tttgtccgaa atacgcgcct actgagtcat tagggacttt ccaatgggtt    4440 tgcccagta cataaggtca atagggggtga atcaacagga aagtcccatt ggagccaagt    4500
acactgagtc aatagggact ttccattggg ttttgcccag tacaaaaggt caataggggg    4560
tgagtcaatg ggttttccc attattggca cgtacataag gtcaataggg gtgagtcatt    4620 gggttttcc agccaattta attaaaacgc catgtacttt cccaccattg acgtcaatgg    4680
gctattgaaa ctaatgcaac gtgacccttta acggtactt tcccatagct gattaatggg    4740
aaagtaccgt tctcgagcca atacacgtca atgggaagtg aaagggcagc caaaacgtaa    4800
caccgccccg gttttcccct ggaaattcca tattggcacg cattctattg gctgagctgc    4860
gttctacgtg ggtataagag gcgcgaccag cgtcggtacc gtcgcagtct cggtctgac    4920 caccgtagaa cgcagcctca ggacctccat agaagacacc gggaccgatc cagcctccgc    4980
ggccgggaac ggtgcattgg aacgcggatt ccccgtgcca agagtgacgt aagtaccgcc    5040
tatagagtct ataggcccac cccccttggct tcttatgcat gctatactgt ttttggcttg    5100
gggtctatac acccccgctt cctcatgtta taggtgatgg tatagcttag cctataggtg    5160
tgggttattg accattattg accactcccc tattggtgac gatactttcc attactaatc    5220
```

```
cataacatgg ctctttgcca caactctctt tattggctat atgccaatac actgtccttc    5280
agagactgac acggactctg tatttttaca ggatggggtc tcatttatta tttacaaatt    5340
cacatataca acaccaccgt ccccagtgcc cgcagttttt attaaacata acgtgggatc    5400
tccacgcgaa tctcgggtac gtgttccgga catgggctct tctccggtag cggcggagct    5460
tctacatccg agccctgctc ccatgcctcc agcgactcat ggtcgctcgg cagctccttg    5520
ctcctaacag tggaggccag acttaggcac agcacgatgc ccaccaccac cagtgtgccg    5580
cacaaggccg tggcggtagg gtatgtgtct gaaaatgagc tcggggagcg ggcttgcacc    5640
gctgacgcat ttggaagact taaggcagcg gcagaagaag atgcaggcag ctgagttgtt    5700
gtgttctgat aagagtcaga ggtaactccc gttgcggtgc tgttaacggt ggagggcagt    5760
gtagtctgag cagtactcgt tgctgccgcg cgcgccacca gacataatag ctgacagact    5820
aacagactgt tcctttccat gggtcttttc tgcagtcacc gtccttgaca cgaagcttac    5880
cggtagatct gctagcacat gtaggcct                                       5908
```

<210> SEQ ID NO 2
<211> LENGTH: 7948
<212> TYPE: DNA
<213> ORGANISM: artificial sequence
<220> FEATURE:
<223> OTHER INFORMATION: plasmid vector pRY57
<220> FEATURE:
<221> NAME/KEY: CDS
<222> LOCATION: (67)..(714)
<223> OTHER INFORMATION: gene optimized cB72.3 kappa light chain
<220> FEATURE:
<221> NAME/KEY: polyA_signal
<222> LOCATION: (720)..(958)
<223> OTHER INFORMATION: SV40 polyA signal
<220> FEATURE:
<221> NAME/KEY: promoter
<222> LOCATION: (979)..(1470)
<223> OTHER INFORMATION: mCMV-MIE (IE1) promoter fragment
<220> FEATURE:
<221> NAME/KEY: 5'UTR
<222> LOCATION: (1471)..(1504)
<223> OTHER INFORMATION: part of mCMV-MIE (IE1) 5'UTR exon 1
<220> FEATURE:
<221> NAME/KEY: 5'UTR
<222> LOCATION: (1516)..(1601)
<223> OTHER INFORMATION: part of hCMV-MIE (IE1) 5'UTR exon 1
<220> FEATURE:
<221> NAME/KEY: Intron
<222> LOCATION: (1598)..(2424)
<223> OTHER INFORMATION: hCMV-MIE (IE1) intron A
<220> FEATURE:
<221> NAME/KEY: 5'UTR
<222> LOCATION: (2425)..(2441)
<223> OTHER INFORMATION: hCMV-MIE (IE1) 5'UTR exon 2
<220> FEATURE:
<221> NAME/KEY: CDS
<222> LOCATION: (2508)..(3836)
<223> OTHER INFORMATION: gene optimized cB72.3 gamma-4 heavy chain
<220> FEATURE:
<221> NAME/KEY: polyA_signal
<222> LOCATION: (3843)..(4081)
<223> OTHER INFORMATION: SV40 polyA signal
<220> FEATURE:
<221> NAME/KEY: promoter
<222> LOCATION: (4095)..(4421)
<223> OTHER INFORMATION: SV40 early promoter, derived from pFRT/lacZeo
      (Invitrogen)
<220> FEATURE:
<221> NAME/KEY: source
<222> LOCATION: (4426)..(4430)
<223> OTHER INFORMATION: sequence containing ATG site found upstream of
      wild-type FRT in pFRT/lacZeo (Invitrogen)
<220> FEATURE:

```
<221> NAME/KEY: misc_recomb
<222> LOCATION: (4431)..(4478)
<223> OTHER INFORMATION: wild-type flippase recognition target (FRT)
      site, derived from pcDNA5-Frt (Invitrogen)
<220> FEATURE:
<221> NAME/KEY: source
<222> LOCATION: (5259)..(6119)
<223> OTHER INFORMATION: reverse complement CDS of beta-lactamase gene
<220> FEATURE:
<221> NAME/KEY: misc_recomb
<222> LOCATION: (6395)..(6442)
<223> OTHER INFORMATION: mutant flippase recognition target (FRT) site
<220> FEATURE:
<221> NAME/KEY: promoter
<222> LOCATION: (6486)..(6977)
<223> OTHER INFORMATION: mCMV-MIE (IE1) promoter fragment
<220> FEATURE:
<221> NAME/KEY: 5'UTR
<222> LOCATION: (6978)..(7011)
<223> OTHER INFORMATION: part of mCMV-MIE (IE1) 5'UTR exon 1
<220> FEATURE:
<221> NAME/KEY: 5'UTR
<222> LOCATION: (7023)..(7108)
<223> OTHER INFORMATION: part of hCMV-MIE (IE1) 5'UTR exon 1
<220> FEATURE:
<221> NAME/KEY: Intron
<222> LOCATION: (7105)..(7931)
<223> OTHER INFORMATION: hCMV-MIE (IE1) intron A
<220> FEATURE:
<221> NAME/KEY: 5'UTR
<222> LOCATION: (7932)..(7948)
<223> OTHER INFORMATION: hCMV-MIE (IE1)5'UTR exon 2

<400> SEQUENCE: 2
aagcttgccg ccaccatgat gcggcctatc gtgctggtgc tgctgttcgc cacctctgcc      60 ctggcc gac atc cag atg acc cag tcc ccc gcc tcc ctg tct gtg tcc        108
       Asp Ile Gln Met Thr Gln Ser Pro Ala Ser Leu Ser Val Ser
       1               5                  10 gtg ggc gag aca gtg acc atc acc tgt cgg gcc tcc gag aac atc tac       156
Val Gly Glu Thr Val Thr Ile Thr Cys Arg Ala Ser Glu Asn Ile Tyr
15                  20                  25                  30 tcc aac ctg gcc tgg tat cag cag aag cag ggc aag tcc cct cag ctg       204
Ser Asn Leu Ala Trp Tyr Gln Gln Lys Gln Gly Lys Ser Pro Gln Leu
                35                  40                  45 ctg gtg tac gcc gcc acc aac ctg gct gac ggc gtg ccc tcc agg ttc       252
Leu Val Tyr Ala Ala Thr Asn Leu Ala Asp Gly Val Pro Ser Arg Phe
            50                  55                  60 tcc ggc tct ggc tcc ggc acc cag tac tcc ctg aag atc aac tcc ctg       300
Ser Gly Ser Gly Ser Gly Thr Gln Tyr Ser Leu Lys Ile Asn Ser Leu
65                  70                  75 cag tcc gag gac ttc ggc tcc tac tac tgc cag cac ttc tgg ggc acc       348
Gln Ser Glu Asp Phe Gly Ser Tyr Tyr Cys Gln His Phe Trp Gly Thr
                80                  85                  90 cct tac acc ttc ggc gga ggc acc cgg ctg gaa atc aag cgg acc gtg       396
Pro Tyr Thr Phe Gly Gly Gly Thr Arg Leu Glu Ile Lys Arg Thr Val
95                  100                 105                 110 gcc gct cct tcc gtg ttc atc ttc cca cct tcc gac gag cag ctg aag       444
Ala Ala Pro Ser Val Phe Ile Phe Pro Pro Ser Asp Glu Gln Leu Lys
                115                 120                 125 tcc ggc acc gcc tct gtg gtg tgc ctg ctg aac aac ttc tac cct cgg       492
Ser Gly Thr Ala Ser Val Val Cys Leu Leu Asn Asn Phe Tyr Pro Arg
            130                 135                 140 gag gcc aag gtg cag tgg aag gtg gac aac gcc ctg cag agc ggc aac       540
Glu Ala Lys Val Gln Trp Lys Val Asp Asn Ala Leu Gln Ser Gly Asn
        145                 150                 155 tcc cag gaa tcc gtc acc gag cag gac tcc aag gac tct acc tac tcc       588
Ser Gln Glu Ser Val Thr Glu Gln Asp Ser Lys Asp Ser Thr Tyr Ser
```

```
                 160                 165                 170
ctg tcc tcc acc ctg acc ctg tcc aag gcc gac tac gag aag cac aag         636
Leu Ser Ser Thr Leu Thr Leu Ser Lys Ala Asp Tyr Glu Lys His Lys
175                 180                 185                 190 gtg tac gcc tgc gaa gtg acc cac cag ggc ctg tcc agc cct gtg acc         684
Val Tyr Ala Cys Glu Val Thr His Gln Gly Leu Ser Ser Pro Val Thr
                    195                 200                 205 aag tcc ttc aac cgg ggc gag tgc tga tag aattcattga tcataatcag           734
Lys Ser Phe Asn Arg Gly Glu Cys
                210 ccataccaca tttgtagagg ttttacttgc tttaaaaaac ctcccacacc tcccccctgaa      794 cctgaaacat aaaatgaatg caattgttgt tgttaacttg tttattgcag cttataatgg       854 ttacaaataa agcaatagca tcacaaattt cacaaataaa gcatttttt cactgcattc        914 tagttgtggt ttgtccaaac tcatcaatgt atcttatcat gtctggcggc cgctgaggcg       974 cgcctactga gtcattaggg actttccaat gggttttgcc cagtacataa ggtcaatagg       1034 ggtgaatcaa caggaaagtc ccattggagc caagtacact gagtcaatag ggactttcca      1094 ttgggttttg cccagtacaa aaggtcaata gggggtgagt caatgggttt tcccattat       1154 tggcacgtac ataaggtcaa tagggtgag tcattgggtt tttccagcca atttaattaa        1214 aacgccatgt actttcccac cattgacgtc aatgggctat tgaaactaat gcaacgtgac      1274 ctttaaacgg tactttccca tagctgatta atggaaagt accgttctcg agccaataca      1334 cgtcaatggg aagtgaaagg cagccaaaa cgtaacaccg ccccggtttt ccctggaaa       1394 ttccatattg gcacgcattc tattggctga gctgcgttct acgtgggtat aagaggcgcg      1454 accagcgtcg gtaccgtcgc agtcttcggt ctgaccaccg tagaacgcag cctcaggacc      1514 tccatagaag acaccgggac cgatccagcc tccgcggccg ggaacggtgc attggaacgc      1574 ggattccccg tgccaagagt gacgtaagta ccgcctatag agtctatagg cccacccccct      1634 tggcttctta tgcatgctat actgttttgt gcttggggtc tatacacccc cgcttcctca      1694 tgttataggt gatggtatag cttagcctat aggtgtgggt tattgaccat tattgaccac      1754 tcccctattg gtgacgatac tttccattac taatccataa catggctctt tgccacaact      1814 ctctttattg gctatatgcc aatacactgt ccttcagaga ctgacacgga ctctgtattt      1874 ttacaggatg gggtctcatt tattatttac aaattcacat atacaacacc accgtcccca      1934 gtgcccgcag tttttattaa acataacgtg gatctccac gcgaatctcg ggtacgtgtt      1994 ccggacatgg gctcttctcc ggtagcggcg gagcttctac atccgagccc tgctcccatg      2054 cctccagcga tcatggtcg ctcggcagct ccttgctcct aacagtggag gccagactta      2114 ggcacagcac gatgcccacc accaccagtg tgccgcacaa ggccgtggcg gtagggtatg      2174 tgtctgaaaa tgagctcggg gagcgggctt gcaccgctga cgcatttgga agacttaagg      2234 cagcggcaga agaagatgca ggcagctgag ttgttgtgtt ctgataagag tcagaggtaa      2294 ctcccgttgc ggtgctgtta acggtggagg gcagtgtagt ctgagcagta ctcgttgctg      2354 ccgcgcgcgc caccagacat aatagctgac agactaacag actgttcctt tccatgggtc      2414 tttttctgcag tcaccgtcct tgacacggga tccgccgcca ccatgatgcg gcctatcgtg      2474 ctggtgctgc tgttcgccac aagcgctctg gct cag gtg cag ctg cag cag agc      2528
                                   Gln Val Gln Leu Gln Gln Ser
                                               215         220 gac gcc gag ctg gtg aag cct ggc gct agc gtg aag atc agc tgc aag         2576
Asp Ala Glu Leu Val Lys Pro Gly Ala Ser Val Lys Ile Ser Cys Lys
                225                 230                 235
```

-continued

| | | |
|---|---|---|
| gcc agc ggc tac acc ttc acc gat cac gcc atc cac tgg gct aag cag<br>Ala Ser Gly Tyr Thr Phe Thr Asp His Ala Ile His Trp Ala Lys Gln<br>240 245 250 | 2624 | |
| aag ccc gag cag ggc ctg gag tgg atc ggc tac atc agc ccc ggc aac<br>Lys Pro Glu Gln Gly Leu Glu Trp Ile Gly Tyr Ile Ser Pro Gly Asn<br>255 260 265 | 2672 | |
| gac gac atc aag tac aac gag aag ttc aag ggc aag gcc acc ctg acc<br>Asp Asp Ile Lys Tyr Asn Glu Lys Phe Lys Gly Lys Ala Thr Leu Thr<br>270 275 280 285 | 2720 | |
| gcc gac aag agc agc agc acc gcc tac atg cag ctg aac agc ctg acc<br>Ala Asp Lys Ser Ser Ser Thr Ala Tyr Met Gln Leu Asn Ser Leu Thr<br>290 295 300 | 2768 | |
| agc gag gac agc gcc gtg tac ttc tgc aag cgg agc tac tac ggc cac<br>Ser Glu Asp Ser Ala Val Tyr Phe Cys Lys Arg Ser Tyr Tyr Gly His<br>305 310 315 | 2816 | |
| tgg ggc cag ggc acc acc ctg aca gtg agc agc gct agc acc aag ggc<br>Trp Gly Gln Gly Thr Thr Leu Thr Val Ser Ser Ala Ser Thr Lys Gly<br>320 325 330 | 2864 | |
| cca agc gtg ttc cca ctg gcc ccc tgc agc aga agc acc agc gag agc<br>Pro Ser Val Phe Pro Leu Ala Pro Cys Ser Arg Ser Thr Ser Glu Ser<br>335 340 345 | 2912 | |
| aca gcc gcc ctg ggc tgc ctg gtg aag gac tac ttc ccc gag ccc gtg<br>Thr Ala Ala Leu Gly Cys Leu Val Lys Asp Tyr Phe Pro Glu Pro Val<br>350 355 360 365 | 2960 | |
| acc gtg tcc tgg aac agc gga gcc ctg aca agc gga gtg cac acc ttc<br>Thr Val Ser Trp Asn Ser Gly Ala Leu Thr Ser Gly Val His Thr Phe<br>370 375 380 | 3008 | |
| ccc gcc gtg ctg cag agc agc ggc ctg tac tcc ctg agc agc gtg gtg<br>Pro Ala Val Leu Gln Ser Ser Gly Leu Tyr Ser Leu Ser Ser Val Val<br>385 390 395 | 3056 | |
| acc gtg cca agc agc agc ctg ggc acc aag acc tac acc tgc aac gtg<br>Thr Val Pro Ser Ser Ser Leu Gly Thr Lys Thr Tyr Thr Cys Asn Val<br>400 405 410 | 3104 | |
| gac cac aag ccc agc aac acc aaa gtg gac aag cgc gtg gag agc aag<br>Asp His Lys Pro Ser Asn Thr Lys Val Asp Lys Arg Val Glu Ser Lys<br>415 420 425 | 3152 | |
| tac ggc cct ccc tgc ccc agc tgt ccc gcc cca gag ttc ctg ggc gga<br>Tyr Gly Pro Pro Cys Pro Ser Cys Pro Ala Pro Glu Phe Leu Gly Gly<br>430 435 440 445 | 3200 | |
| ccc tca gtg ttt ctg ttc cca ccc aag ccc aag gat acc ctg atg atc<br>Pro Ser Val Phe Leu Phe Pro Pro Lys Pro Lys Asp Thr Leu Met Ile<br>450 455 460 | 3248 | |
| agc cgg acc cct gaa gtg acc tgc gtg gtg gtg gat gtg agc cag gag<br>Ser Arg Thr Pro Glu Val Thr Cys Val Val Val Asp Val Ser Gln Glu<br>465 470 475 | 3296 | |
| gac ccc gaa gtc cag ttc aat tgg tac gtg gac ggc gtg gaa gtg cac<br>Asp Pro Glu Val Gln Phe Asn Trp Tyr Val Asp Gly Val Glu Val His<br>480 485 490 | 3344 | |
| aac gcc aag acc aag ccc aga gag gag cag ttc aac agc acc tac cgc<br>Asn Ala Lys Thr Lys Pro Arg Glu Glu Gln Phe Asn Ser Thr Tyr Arg<br>495 500 505 | 3392 | |
| gtg gtg tct gtg ctg acc gtg ctg cac cag gat tgg ctg aac ggc aaa<br>Val Val Ser Val Leu Thr Val Leu His Gln Asp Trp Leu Asn Gly Lys<br>510 515 520 525 | 3440 | |
| gag tac aag tgc aag gtc tcc aac aag ggc ctg cct agc agc atc gag<br>Glu Tyr Lys Cys Lys Val Ser Asn Lys Gly Leu Pro Ser Ser Ile Glu<br>530 535 540 | 3488 | |
| aaa acc atc agc aag gcc aag ggc cag cca cgc gag ccc cag gtg tac<br>Lys Thr Ile Ser Lys Ala Lys Gly Gln Pro Arg Glu Pro Gln Val Tyr | 3536 | |

```
                545                  550                  555
acc ctg ccc ccc agc caa gag gag atg acc aag aac cag gtg tcc ctg      3584
Thr Leu Pro Pro Ser Gln Glu Glu Met Thr Lys Asn Gln Val Ser Leu
            560                  565                  570 acc tgt ctg gtg aag ggc ttc tac ccc agc gac atc gcc gtg gag tgg      3632
Thr Cys Leu Val Lys Gly Phe Tyr Pro Ser Asp Ile Ala Val Glu Trp
    575                  580                  585 gag agc aac ggc cag ccc gag aac aac tac aag acc acc ccc cct gtg      3680
Glu Ser Asn Gly Gln Pro Glu Asn Asn Tyr Lys Thr Thr Pro Pro Val
590                  595                  600                  605 ctg gac agc gat ggc agc ttc ttc ctg tac tca cgg ctg acc gtg gat      3728
Leu Asp Ser Asp Gly Ser Phe Phe Leu Tyr Ser Arg Leu Thr Val Asp
                610                  615                  620 aag agc aga tgg caa gag ggc aat gtc ttt agc tgc agc gtg atg cac      3776
Lys Ser Arg Trp Gln Glu Gly Asn Val Phe Ser Cys Ser Val Met His
            625                  630                  635 gag gcc ctg cac aat cct aca ccc aga aga gcc tga gcc tgt ccc ctg      3824
Glu Ala Leu His Asn Pro Thr Pro Arg Arg Ala     Ala Cys Pro Leu
            640                  645                       650 ggc aag tga tag tcgcgaattg atcataatca gccataccac atttgtagag          3876
Gly Lys gttttacttg ctttaaaaaa cctcccacac ctcccctga acctgaaaca taaaatgaat     3936
gcaattgttg ttgttaactt gtttattgca gcttataatg gttacaaata agcaatagc     3996
atcacaaatt tcacaaataa agcatttttt tcactgcatt ctagttgtgg tttgtccaaa    4056
ctcatcaatg tatcttatca tgtctggatc agcttgagca gctgtggaat gtgtgtcagt    4116
tagggtgtgg aaagtcccca ggctccccag caggcagaag tatgcaaagc atgcatctca    4176
attagtcagc aaccaggtgt ggaaagtccc caggctcccc agcaggcaga agtatgcaaa    4236
gcatgcatct caattagtca gcaaccatag tcccgcccct aactccgccc atcccgcccc    4296
taactccgcc cagttccgcc cattctccgc cccatggctg actaatttttt tttatttatg   4356
cagaggccga ggccgcctcg gcctctgagc tattccagaa gtagtgagga ggcttttttg    4416
gaggctacca tggagaagtt actattccga agttcctatt ctctagaaag tataggaact    4476
tctcgggccg cgttgctggc gttttttccat aggctccgcc ccctgacga gcatcacaaa    4536
aatcgacgct caagtcagag gtggcgaaac ccgacaggac tataaagata ccaggcgttt    4596
cccccctggaa gctccctcgt gcgctctcct gttccgaccc tgccgcttac cggatacctg   4656
tccgcctttc tcccttcggg aagcgtggcg ctttctcata gctcacgctg taggtatctc    4716
agttcggtgt aggtcgttcg ctccaagctg ggctgtgtgc acgaaccccc cgttcagccc    4776
gaccgctgcg ccttatccgg taactatcgt cttgagtcca acccggtaag acacgactta    4836
tcgccactgg cagcagccac tggtaacagg attagcagag cgaggtatgt aggcggtgct    4896
acagagttct tgaagtggtg gcctaactac ggctacacta agaacagt attttggtatc     4956
tgcgctctgc tgaagccagt taccttcgga aaaagagttg gtagctcttg atccggcaaa    5016
caaaccaccg ctggtagcgg tggttttttt gtttgcaagc agcagattac gcgcagaaaa    5076
aaaggatctc aagaagatcc tttgatcttt tctacggggt ctgacgctca gtggaacgaa    5136
aactcacgtt aagggatttt ggtcatgaga ttatcaaaaa ggatcttcac ctagatcctt    5196
ttaaattaaa aatgaagttt taaatcaatc taaagtatat atgagtaaac ttggtctgac    5256
agttaccaat gcttaatcag tgaggcacct atctcagcga tctgtctatt tcgttcatcc    5316
atagttgcct gactccccgt cgtgtagata actacgatac gggagggctt accatctggc    5376
```

```
cccagtgctg caatgatacc gcgagaccca cgctcaccgg ctccagattt atcagcaata    5436
aaccagccag ccggaagggc cgagcgcaga agtggtcctg caactttatc cgcctccatc    5496
cagtctatta attgttgccg ggaagctaga gtaagtagtt cgccagttaa tagtttgcgc    5556
aacgttgttg ccattgctac aggcatcgtg tgtcacgct cgtcgtttgg tatggcttca     5616
ttcagctccg gttcccaacg atcaaggcga gttacatgat cccccatgtt gtgcaaaaaa    5676
gcggttagct ccttcggtcc tccgatcgtt gtcagaagta agttggccgc agtgttatca    5736
ctcatggtta tggcagcact gcataattct cttactgtca tgccatccgt aagatgcttt    5796
tctgtgactg gtgagtactc aaccaagtca ttctgagaat agtgtatgcg gcgaccgagt    5856
tgctcttgcc cggcgtcaat acgggataat accgcgccac atagcagaac tttaaaagtg    5916
ctcatcattg gaaaacgttc ttcggggcga aaactctcaa ggatcttacc gctgttgaga    5976
tccagttcga tgtaacccac tcgtgcaccc aactgatctt cagcatcttt tactttcacc    6036
agcgtttctg ggtgagcaaa aacaggaagg caaaatgccg caaaaaaggg aataagggcg    6096
acacggaaat gttgaatact catactcttc ctttttcaat attattgaag catttatcag    6156
ggttattgtc tcatgagcgg atacatattt gaatgtattt agaaaaataa acaaatagggg   6216
gttccgcgca catttccccg aaaagtgcca cctgacgtct aagaaaccat tattatcatg    6276
acattaacct ataaaaatag gcgtatcacg aggccctgat ggctctttgc ggcacccatc    6336
gttcgtaatg ttccgtggca ccgaggacaa ccctcaagag aaaatgtaat cacactggga    6396
agttcctatt ccgaagttcc tattcttcaa aaggtatagg aacttcctgc agtgaataat    6456
aaaatgtgtg tttgtccgaa atacgcgcct actgagtcat tagggacttt ccaatgggtt    6516
ttgcccagta cataaggtca ataggggtga atcaacagga aagtcccatt ggagccaagt    6576
acactgagtc aatagggact ttccattggg ttttgcccag tacaaaaggt caataggggg    6636
tgagtcaatg ggttttttcc attattggca cgtacataag gtcaataggg gtgagtcatt    6696
gggttttttcc agccaattta attaaaaacgc catgtacttt cccaccattg acgtcaatgg    6756
gctattgaaa ctaatgcaac gtgacccttta aacggtactt tcccatagct gattaatggg    6816
aaagtaccgt tctcgagcca atacacgtca atgggaagtg aaagggcagc caaaacgtaa    6876
caccgccccg gttttcccct ggaaattcca tattggcacg cattctattg gctgagctgc    6936
gttctacgtg ggtataagag gcgcgaccag cgtcggtacc gtcgcagtct tcggtctgac    6996
caccgtagaa cgcagcctca ggacctccat agaagacacc gggaccgatc cagcctccgc    7056
ggccgggaac ggtgcattgg aacgcggatt cccccgtgcca agagtgacgt aagtaccgcc    7116
tatagagtct ataggcccac ccccttggct tcttatgcat gctatactgt ttttggcttg    7176
gggtctatac accccccgctt cctcatgtta taggtgatgg tatagcttag cctataggtg    7236
tgggttattg accattattg accactcccc tattggtgac gatactttcc attactaatc    7296
cataacatgg ctcttttgcca caactctctt tattggctat atgccaatac actgtccttc    7356
agagactgac acggactctg tattttttaca ggatggggtc tcatttatta tttacaaatt    7416
cacatataca acaccaccgt ccccagtgcc cgcagttttt attaaacata acgtgggatc    7476
tccacgcgaa tctcgggtac gtgttccgga catgggctct tctccggtag cggcggagct    7536
tctacatccg agccctgctc ccatgcctcc agcgactcat ggtcgctcgg cagctccttg    7596
ctcctaacag tggaggccag acttaggcac agcacgatgc ccaccaccac cagtgtgccg    7656
cacaaggccg tggcggtagg gtatgtgtct gaaaatgagc tcggggagcg ggcttgcacc    7716
gctgacgcat ttggaagact taaggcagcg gcagaagaag atgcaggcag ctgagttgtt    7776
```

```
gtgttctgat aagagtcaga ggtaactccc gttgcggtgc tgttaacggt ggagggcagt    7836
gtagtctgag cagtactcgt tgctgccgcg cgcgccacca gacataatag ctgacagact    7896
aacagactgt tcctttccat gggtcttttc tgcagtcacc gtccttgaca cg            7948
```

<210> SEQ ID NO 3
<211> LENGTH: 492
<212> TYPE: DNA
<213> ORGANISM: artificial sequence
<220> FEATURE:
<223> OTHER INFORMATION: fragment of the mCMV IE1 promoter sequence

<400> SEQUENCE: 3

```
tactgagtca ttagggactt tccaatgggt tttgcccagt acataaggtc aatagggtg     60 aatcaacagg aaagtcccat ggagccaagt acactgagt caatagggac ttccattgg     120 gttttgccca gtacaaaagg tcaataggg gtgagtcaat gggttttttcc cattattggc   180 acgtacataa ggtcaatagg ggtgagtcat gggttttttc cagccaattt aattaaaacg   240
ccatgtactt tcccaccatt gacgtcaatg gctattgaa actaatgcaa cgtgaccttt    300
aaacggtact ttcccatagc tgattaatgg gaaagtaccg ttctcgagcc aatacacgtc   360
aatgggaagt gaaagggcag ccaaaacgta acaccgcccc ggttttcccc tggaaattcc   420
atattggcac gcattctatt ggctgagctg cgttctacgt gggtataaga ggcgcgacca   480
gcgtcggtac cg                                                        492
```

<210> SEQ ID NO 4
<211> LENGTH: 102
<212> TYPE: DNA
<213> ORGANISM: artificial sequence
<220> FEATURE:
<223> OTHER INFORMATION: fragment of the mCMV IE1 promoter sequence
        ("core promoter")

<400> SEQUENCE: 4

```
acaccgcccc ggttttcccc tggaaattcc atattggcac gcattctatt ggctgagctg    60
cgttctacgt gggtataaga ggcgcgacca gcgtcggtac cg                      102
```

<210> SEQ ID NO 5
<211> LENGTH: 117
<212> TYPE: DNA
<213> ORGANISM: artificial sequence
<220> FEATURE:
<223> OTHER INFORMATION: fragment of the hCMV IE1 promoter sequence
        ("core promoter")

<400> SEQUENCE: 5

```
gcaccaaaat caacgggact ttccaaaatg tcgtaacaac tccgccccat tgacgcaaat    60
gggcggtagg cgtgtacggt gggaggtcta tataagcaga gctcgtttag tgaaccg      117
```

<210> SEQ ID NO 6
<211> LENGTH: 452
<212> TYPE: DNA
<213> ORGANISM: artificial sequence
<220> FEATURE:
<223> OTHER INFORMATION: fragment of the sCMV IE1 enhancer sequence

<400> SEQUENCE: 6

```
gaccatagcc aattcaatat ggcgtatatg gactcatgcc aattcaatat ggtggatctg    60
gacctgtgcc aattcaatat ggcgtatatg gactcgtgcc aattcaatat ggtggatctg   120
```

```
gaccccagcc aattcaatat ggcggacttg gcaccatgcc aattcaatat ggcggacctg      180
gcactgtgcc aactggggag gggtctactt ggcacggtgc caagtttgag gagggtgctt      240
ggccctgtgc caagtccgcc atattgaatt ggcatggtgc caataatggc ggccatattg      300
gctatatgcc aggatcaata taggcaat atccaatatg gccctatgcc aatatggcta       360
ttggccaggt tcaatactat gtattggccc tatgccatat agtattccat atatgggttt      420
tcctattgac gtagatagcc cctcccaatg gg                                    452
```

```
<210> SEQ ID NO 7
<211> LENGTH: 1074
<212> TYPE: DNA
<213> ORGANISM: artificial sequence
<220> FEATURE:
<223> OTHER INFORMATION: chimeric 5'-untranslated regulatory sequence
      ("construct 1")
<220> FEATURE:
<221> NAME/KEY: enhancer
<222> LOCATION: (1)..(582)
<223> OTHER INFORMATION: fragment of hCMV IE1 and mCMV IE1 enhancer
      sequence
<220> FEATURE:
<221> NAME/KEY: promoter
<222> LOCATION: (583)..(1074)
<223> OTHER INFORMATION: fragment of mCMV IE1 promoter sequence

<400> SEQUENCE: 7
```

```
ctgcagtgaa taataaaatg tgtgtttgtc cgaaatacgc gttttgagat ttctgtcgcc      60
gactaaattc atgtcgcgcg atagtggtgt ttatcgccga tagagatggc gatattggaa     120
aaatcgatat ttgaaaatat ggcatattga aaatgtcgcc gatgtgagtt tctgtgtaac     180
tgatatcgcc attttttccaa aagtgatttt tgggcatacg cgatatctgg cgatagcgct     240
tatatcgttt acggggatg gcgatagacg actttggtga cttgggcgat tctgtgtgtc      300
gcaaatatcg cagtttcgat ataggtgaca gacgatatga ggctatatcg ccgatagagg     360
cgacatcaag ctggcacatg gccaatgcat atcgatctat acattgaatc aatattggcc     420
attagccata ttattcattg gttatatagc ataaatcaat attggctatt ggccattgca     480
tacgttgtat ccatatcata atatgtacat ttatattggc tcatgtccaa cattaccgcc     540
atgttgacat tgattattga ctagttatta atagtaatca attactgagt cattagggac     600
tttccaatgg gttttgccca gtacataagg tcaataggg tgaatcaaca ggaaagtccc     660
attggagcca agtacactga gtcaataggg actttccatt gggttttgcc cagtacaaaa     720 ggtcaataggg gggtgagtca atgggttttt cccattattg gcacgtacat aaggtcaata     780
ggggtgagtc attgggtttt tccagccaat ttaattaaaa cgccatgtac tttcccacca     840
ttgacgtcaa tgggctattg aaactaatgc aacgtgacct ttaaacggta ctttcccata     900
gctgattaat gggaaagtac cgttctcgag ccaatacacg tcaatgggaa gtgaagggc     960 agccaaaacg taacaccgcc ccggttttcc cctggaaatt ccatattggc acgcattcta    1020
ttggctgagc tgcgttctac gtgggtataa gaggcgcgac cagcgtcggt accg          1074
```

```
<210> SEQ ID NO 8
<211> LENGTH: 1128
<212> TYPE: DNA
<213> ORGANISM: artificial sequence
<220> FEATURE:
<223> OTHER INFORMATION: chimeric 5'-untranslated regulatory sequence
      ("construct 2")
<220> FEATURE:
<221> NAME/KEY: enhancer
<222> LOCATION: (1)..(1026)
```

<223> OTHER INFORMATION: fragment of hCMV IE1 enhancer sequence
<220> FEATURE:
<221> NAME/KEY: promoter
<222> LOCATION: (1027)..(1128)
<223> OTHER INFORMATION: fragment of mCMV IE1 promoter sequence ("core promoter")

<400> SEQUENCE: 8

```
ctgcagtgaa taataaaatg tgtgtttgtc cgaaatacgc gttttgagat ttctgtcgcc      60
gactaaattc atgtcgcgcg atagtggtgt ttatcgccga tagagatggc gatattggaa     120
aaatcgatat ttgaaaatat ggcatattga aaatgtcgcc gatgtgagtt tctgtgtaac     180
tgatatcgcc attttccaa aagtgatttt tgggcatacg cgatatctgg cgatagcgct      240
tatatcgttt acggggatg gcgatagacg actttggtga cttgggcgat tctgtgtgtc      300
gcaaatatcg cagtttcgat ataggtgaca gacgatatga ggctatatcg ccgatagagg     360
cgacatcaag ctggcacatg gccaatgcat atcgatctat acattgaatc aatattggcc     420
attagccata ttattcattg gttatatagc ataaatcaat attggctatt ggccattgca     480
tacgttgtat ccatatcata atatgtacat ttatattggc tcatgtccaa cattaccgcc     540
atgttgacat tgattattga ctagttatta atagtaatca attacggggt cattagttca     600
tagcccatat atggagttcc gcgttacata acttacggta aatggcccgc ctggctgacc     660
gcccaacgac ccccgcccat tgacgtcaat aatgacgtat gttcccatag taacgccaat     720
agggactttc cattgacgtc aatgggtgga gtatttacgg taaactgccc acttggcagt     780
acatcaagtg tatcatatgc caagtacgcc cctattgac gtcaatgacg gtaaatggcc      840
cgcctggcat tatgcccagt acatgacctt atgggacttt cctacttggc agtacatcta     900
cgtattagtc atcgctatta ccatggtgat gcggttttgg cagtacatca atgggcgtgg     960
atagcggttt gactcacggg gatttccaag tctccacccc attgacgtca atgggagttt    1020
gttttgacac cgccccggtt ttcccctgga aattccatat tggcacgcat tctattggct    1080
gagctgcgtt ctacgtgggt ataagaggcg cgaccagcgt cggtaccg                 1128
```

<210> SEQ ID NO 9
<211> LENGTH: 509
<212> TYPE: DNA
<213> ORGANISM: artificial sequence
<220> FEATURE:
<223> OTHER INFORMATION: chimeric 5'-untranslated regulatory sequence ("construct 3")
<220> FEATURE:
<221> NAME/KEY: enhancer
<222> LOCATION: (1)..(407)
<223> OTHER INFORMATION: fragment of hCMV IE1 enhancer sequence
<220> FEATURE:
<221> NAME/KEY: promoter
<222> LOCATION: (408)..(509)
<223> OTHER INFORMATION: fragment of mCMV IE1 promoter sequence ("core promoter")

<400> SEQUENCE: 9

```
cgcgttacat aacttacggt aaatggcccg cctggctgac cgcccaacga ccccgcccca     60
ttgacgtcaa taatgacgta tgttcccata gtaacgccaa tagggacttt ccattgacgt    120
caatgggtgg agtatttacg gtaaactgcc cacttggcag tacatcaagt gtatcatatg    180
ccaagtacgc ccctattga cgtcaatgac ggtaaatggc cgcctggca ttatgcccag     240
tacatgacct tatgggactt tcctacttgg cagtacatct acgtattagt catcgctatt    300
accatggtga tgcggttttg cagtacatc aatgggcgtg gatagcggtt tgactcacgg    360
```

```
ggatttccaa gtctccaccc cattgacgtc aatgggagtt tgttttgaca ccgcccggt      420 tttcccctgg aaattccata ttggcacgca ttctattggc tgagctgcgt tctacgtggg      480
tataagaggc gcgaccagcg tcggtaccg                                        509

<210> SEQ ID NO 10
<211> LENGTH: 961
<212> TYPE: DNA
<213> ORGANISM: artificial sequence
<220> FEATURE:
<223> OTHER INFORMATION: chimeric 5'-untranslated regulatory sequence
      ("construct 4")
<220> FEATURE:
<221> NAME/KEY: enhancer
<222> LOCATION: (1)..(452)
<223> OTHER INFORMATION: fragment of sCMV IE1 enhancer sequence
<220> FEATURE:
<221> NAME/KEY: enhancer
<222> LOCATION: (453)..(859)
<223> OTHER INFORMATION: fragment of hCMV IE1 enhancer sequence
<220> FEATURE:
<221> NAME/KEY: promoter
<222> LOCATION: (860)..(961)
<223> OTHER INFORMATION: fragment of mCMV IE1 promoter sequence ("core
      promoter")

<400> SEQUENCE: 10
gaccatagcc aattcaatat ggcgtatatg gactcatgcc aattcaatat ggtggatctg      60
gacctgtgcc aattcaatat ggcgtatatg gactcgtgcc aattcaatat ggtggatctg      120
gaccccagcc aattcaatat ggcggacttg gcaccatgcc aattcaatat ggcggacctg      180
gcactgtgcc aactggggag gggtctactt ggcacggtgc caagtttgag gaggggtctt      240
ggccctgtgc caagtccgcc atattgaatt ggcatggtgc caataatggc ggccatattg      300
gctatatgcc aggatcaata taggcaat atccaatatg gccctatgcc aatatggcta       360
ttggccaggt tcaatactat gtattggccc tatgccatat agtattccat atatgggttt      420
tcctattgac gtagatagcc cctcccaatg ggcgcgttac ataacttacg gtaaatggcc      480
cgcctggctg accgcccaac gacccccgcc cattgacgtc aataatgacg tatgttccca      540
tagtaacgcc aatagggact ttccattgac gtcaatgggt ggagtattta cgtaaactg       600 cccacttggc agtacatcaa gtgtatcata tgccaagtac gcccctatt gacgtcaatg       660 acggtaaatg gcccgcctgg cattatgccc agtacatgac cttatgggac tttcctactt      720
ggcagtacat ctacgtatta gtcatcgcta ttaccatggt gatgcggttt tggcagtaca      780
tcaatgggcg tggatagcgg tttgactcac ggggatttcc aagtctccac cccattgacg      840
tcaatgggag tttgttttga caccgcccg gttttcccct ggaaattcca tattggcacg       900
cattctattg gctgagctgc gttctacgtg ggtataagag gcgcgaccag cgtcggtacc      960
g                                                                     961

<210> SEQ ID NO 11
<211> LENGTH: 909
<212> TYPE: DNA
<213> ORGANISM: artificial sequence
<220> FEATURE:
<223> OTHER INFORMATION: chimeric 5'-untranslated regulatory sequence
      ("construct 5")
<220> FEATURE:
<221> NAME/KEY: enhancer
<222> LOCATION: (1)..(807)
<223> OTHER INFORMATION: fragment of sCMV IE1 enhancer sequence
<220> FEATURE:
<221> NAME/KEY: promoter
<222> LOCATION: (808)..(909)
```

-continued

<223> OTHER INFORMATION: fragment of mCMV IE1 promoter sequence ("core promoter")

<400> SEQUENCE: 11

```
gaccatagcc aattcaatat ggcgtatatg gactcatgcc aattcaatat ggtggatctg    60
gacctgtgcc aattcaatat ggcgtatatg gactcgtgcc aattcaatat ggtggatctg   120
gaccccagcc aattcaatat ggcggacttg gcaccatgcc aattcaatat ggcggacctg   180
gcactgtgcc aactggggag gggtctactt ggcacggtgc caagtttgag gagggtctt    240
ggccctgtgc caagtccgcc atattgaatt ggcatggtgc caataatggc ggccatattg   300
gctatatgcc aggatcaata tataggcaat atccaatatg gccctatgcc aatatggcta   360
ttggccaggt tcaatactat gtattggccc tatgccatat agtattccat atatgggttt   420
tcctattgac gtagatagcc cctcccaatg ggcggtccca taccatat atggggcttc     480
ctaataccgc ccatagccac tcccccattg acgtcaatgg tctctatata tggtctttcc   540
tattgacgtc atatgggcgg tcctattgac gtatatggcg cctcccccat tgacgtcaat   600
tacggtaaat ggcccgcctg gctcaatgcc cattgacgtc aataggacca cccaccattg   660
acgtcaatgg gatggctcat tgcccattca tatccgttct cacgccccct attgacgtca   720
atgacggtaa atggcccact tggcagtaca tcaatatcta ttaatagtaa cttggcaagt   780
acattactat tggaagtacg ccagggtaca ccgccccggt tttcccctgg aaattccata   840
ttggcacgca ttctattggc tgagctgcgt tctacgtggg tataagaggc gcgaccagcg   900
tcggtaccg                                                            909
```

<210> SEQ ID NO 12
<211> LENGTH: 976
<212> TYPE: DNA
<213> ORGANISM: artificial sequence
<220> FEATURE:
<223> OTHER INFORMATION: chimeric 5'-untranslated regulatory sequence ("construct 6")
<220> FEATURE:
<221> NAME/KEY: enhancer
<222> LOCATION: (1)..(452)
<223> OTHER INFORMATION: fragment of sCMV IE1 enhancer sequence
<220> FEATURE:
<221> NAME/KEY: enhancer
<222> LOCATION: (453)..(859)
<223> OTHER INFORMATION: fragment of hCMV IE1 enhancer sequence
<220> FEATURE:
<221> NAME/KEY: promoter
<222> LOCATION: (860)..(976)
<223> OTHER INFORMATION: fragment of hCMV IE1 promoter sequence ("core promoter")

<400> SEQUENCE: 12

```
gaccatagcc aattcaatat ggcgtatatg gactcatgcc aattcaatat ggtggatctg    60
gacctgtgcc aattcaatat ggcgtatatg gactcgtgcc aattcaatat ggtggatctg   120
gaccccagcc aattcaatat ggcggacttg gcaccatgcc aattcaatat ggcggacctg   180
gcactgtgcc aactggggag gggtctactt ggcacggtgc caagtttgag gagggtctt    240
ggccctgtgc caagtccgcc atattgaatt ggcatggtgc caataatggc ggccatattg   300
gctatatgcc aggatcaata tataggcaat atccaatatg gccctatgcc aatatggcta   360
ttggccaggt tcaatactat gtattggccc tatgccatat agtattccat atatgggttt   420
tcctattgac gtagatagcc cctcccaatg ggcgcgttac ataacttacg gtaaatggcc   480
cgcctggctg accgcccaac gaccccgcc cattgacgtc aataatgacg tatgttccca   540
```

```
tagtaacgcc aatagggact ttccattgac gtcaatgggt ggagtattta cggtaaactg      600
cccacttggc agtacatcaa gtgtatcata tgccaagtac gccccctatt gacgtcaatg      660
acggtaaatg gcccgcctgg cattatgccc agtacatgac cttatgggac tttcctactt      720
ggcagtacat ctacgtatta gtcatcgcta ttaccatggt gatgcggttt tggcagtaca      780
tcaatgggcg tggatagcgg tttgactcac ggggatttcc aagtctccac cccattgacg      840
tcaatgggag tttgttttgg caccaaaatc aacgggactt tccaaaatgt cgtaacaact      900
ccgccccatt gacgcaaatg ggcggtaggc gtgtacggtg gaggtctat  ataagcagag      960 ctcgtttagt gaaccg                                                      976
```

```
<210> SEQ ID NO 13
<211> LENGTH: 924
<212> TYPE: DNA
<213> ORGANISM: artificial sequence
<220> FEATURE:
<223> OTHER INFORMATION: chimeric 5'-untranslated regulatory sequence
      ("construct 7")
<220> FEATURE:
<221> NAME/KEY: enhancer
<222> LOCATION: (1)..(807)
<223> OTHER INFORMATION: fragment of sCMV IE1 enhancer sequence
<220> FEATURE:
<221> NAME/KEY: promoter
<222> LOCATION: (808)..(924)
<223> OTHER INFORMATION: fragment of hCMV IE1 promoter sequence ("core
      promoter")

<400> SEQUENCE: 13
```

```
gaccatagcc aattcaatat ggcgtatatg gactcatgcc aattcaatat ggtggatctg       60
gacctgtgcc aattcaatat ggcgtatatg gactcgtgcc aattcaatat ggtggatctg      120
gaccccagcc aattcaatat ggcggacttg gcaccatgcc aattcaatat ggcggacctg      180
gcactgtgcc aactggggag gggtctactt ggcacggtgc caagtttgag gagggtctt       240 ggccctgtgc caagtccgcc atattgaatt ggcatggtgc caataatggc ggccatattg      300
gctatatgcc aggatcaata taggcaat atccaatatg gccctatgcc aatatggcta       360
ttggccaggt tcaatactat gtattggccc tatgccatat agtattccat atatgggttt      420
tcctattgac gtagatagcc cctcccaatg ggcggtccca tataccatat atggggcttc      480
ctaataccgc ccatagccac tcccccattg acgtcaatgg tctctatata tggtctttcc      540
tattgacgtc atatgggcgg tcctattgac gtatatggcg cctcccccat tgacgtcaat      600
tacggtaaat ggcccgcctg gctcaatgcc cattgacgtc aataggacca cccaccattg      660
acgtcaatgg gatggctcat tgcccattca tatccgttct cacgcccct  attgacgtca      720 atgacggtaa atggcccact tggcagtaca tcaatatcta ttaatagtaa cttggcaagt      780
acattactat tggaagtacg ccagggtgca ccaaaatcaa cgggactttc caaaatgtcg      840
taacaactcc gccccattga cgcaaatggg cggtaggcgt gtacggtggg aggtctatat      900
aagcagagct cgtttagtga accg                                             924
```

```
<210> SEQ ID NO 14
<211> LENGTH: 214
<212> TYPE: PRT
<213> ORGANISM: artificial sequence
<220> FEATURE:
<223> OTHER INFORMATION: optimized cB72.3 kappa light chain

<400> SEQUENCE: 14

Asp Ile Gln Met Thr Gln Ser Pro Ala Ser Leu Ser Val Ser Val Gly
```

```
                1               5                   10                  15
           Asp Thr Val Thr Ile Thr Cys Arg Ala Ser Glu Asn Ile Tyr Ser Asn
                           20                  25                  30
           Leu Ala Trp Tyr Gln Lys Gln Gly Lys Ser Pro Gln Leu Leu Val
                       35                  40                  45
           Tyr Ala Ala Thr Asn Leu Ala Asp Gly Val Pro Ser Arg Phe Ser Gly
                       50                  55                  60
           Ser Gly Ser Gly Thr Gln Tyr Ser Leu Lys Ile Asn Ser Leu Gln Ser
           65                  70                  75                  80
           Glu Asp Phe Gly Ser Tyr Tyr Cys Gln His Phe Trp Gly Thr Pro Tyr
                               85                  90                  95
           Thr Phe Gly Gly Gly Thr Arg Leu Glu Ile Lys Arg Thr Val Ala Ala
                           100                 105                 110
           Pro Ser Val Phe Ile Phe Pro Pro Ser Asp Glu Gln Leu Lys Ser Gly
                           115                 120                 125
           Thr Ala Ser Val Val Cys Leu Leu Asn Asn Phe Tyr Pro Arg Glu Ala
                       130                 135                 140
           Lys Val Gln Trp Lys Val Asp Asn Ala Leu Gln Ser Gly Asn Ser Gln
           145                 150                 155                 160
           Asp Ser Val Thr Glu Gln Asp Ser Lys Asp Ser Thr Tyr Ser Leu Ser
                               165                 170                 175
           Ser Thr Leu Thr Leu Ser Lys Ala Asp Tyr Glu Lys His Lys Val Tyr
                           180                 185                 190
           Ala Cys Glu Val Thr His Gln Gly Leu Ser Ser Pro Val Thr Lys Ser
                       195                 200                 205
           Phe Asn Arg Gly Glu Cys
                       210

<210> SEQ ID NO 15
<211> LENGTH: 434
<212> TYPE: PRT
<213> ORGANISM: artificial sequence
<220> FEATURE:
<223> OTHER INFORMATION: optimized cB72.3 gamma-4 heavy chain

<400> SEQUENCE: 15

Gln Val Gln Leu Gln Gln Ser Asp Ala Glu Leu Val Lys Pro Gly Ala
           1               5                   10                  15
           Ser Val Lys Ile Ser Cys Lys Ala Ser Gly Tyr Thr Phe Thr Asp His
                           20                  25                  30
           Ala Ile His Trp Ala Lys Gln Lys Pro Glu Gln Gly Leu Glu Trp Ile
                       35                  40                  45
           Gly Tyr Ile Ser Pro Gly Asn Asp Asp Ile Lys Tyr Asn Glu Lys Phe
                       50                  55                  60
           Lys Gly Lys Ala Thr Leu Thr Ala Asp Lys Ser Ser Ser Thr Ala Tyr
           65                  70                  75                  80
           Met Gln Leu Asn Ser Leu Thr Ser Glu Asp Ser Ala Val Tyr Phe Cys
                               85                  90                  95
           Lys Arg Ser Tyr Tyr Gly His Trp Gly Gln Gly Thr Thr Leu Thr Val
                           100                 105                 110
           Ser Ser Ala Ser Thr Lys Gly Pro Ser Val Phe Pro Leu Ala Pro Cys
                           115                 120                 125
           Ser Arg Ser Thr Ser Glu Ser Thr Ala Ala Leu Gly Cys Leu Val Lys
                       130                 135                 140
           Glu Tyr Phe Pro Glu Pro Val Thr Val Ser Trp Asn Ser Gly Ala Leu
```

```
145                 150                 155                 160
Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
                180                 185                 190

Lys Thr Tyr Thr Cys Asn Val Asp His Lys Pro Ser Asn Thr Lys Val
            195                 200                 205

Asp Lys Arg Val Glu Ser Lys Tyr Gly Pro Pro Cys Pro Ser Cys Pro
        210                 215                 220

Ala Pro Glu Glu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
                260                 265                 270

Val Asp Gly Val Glu Val His Asn Ala Lys Thr Lys Pro Arg Glu Glu
                275                 280                 285

Gln Phe Asn Ser Thr Tyr Arg Val Val Ser Val Leu Thr Val Leu His
        290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
                340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn Pro Thr Pro Arg
                420                 425                 430

Arg Ala
```

EXPRESSION VECTORS COMPRISING CHIMERIC CYTOMEGALOVIRUS PROMOTER AND ENHANCER SEQUENCES

PRIORITY CLAIM

This application is a divisional of U.S. application Ser. No. 14/426,329, filed Mar. 5, 2014, now Issued as U.S. Pat. No. 9,777,290, which is a national stage entry of PCT/EP2013/069715, filed Sep. 23, 2013, each of which are incorporated herein by reference in their entireties.

FIELD OF THE INVENTION

The present invention relates to mammalian expression systems, and in particular to expression constructs comprising chimeric promoter regulatory sequences for the heterologous expression of a nucleic acid sequence of interest in mammalian cells. The chimeric promoter regulatory sequences are composed of a promoter sequence derived from murine or from human cytomegalovirus and an upstream region and/or enhancer sequence derived from human and/or simian cytomegalovirus provided that the sequence elements are derived from at least two different cytomegalovirus species.

BACKGROUND

Recombinant (poly)peptides and proteins for applications in basic research, diagnostics, and therapy, such as antibody molecules, vaccines, hormones, and growth factors, are produced using a wide variety of genetically engineered organisms that include both prokaryotic and eukaryotic cells. However, the vast majority of recombinant peptides or proteins include post-translational modifications that cannot be mimicked or re-produced when using prokaryotic host cells. For this reason, mammalian gene expression systems have turned out to represent a preferred choice.

Mammalian expression systems based on Chinese Hamster ovary (CHO) cells are widely used in production of recombinant protein. Apart from lymphoid cell lines, CHO cells represent one of the few cell types allowing for simple and efficient high-density suspension batch culture of animal cells. Furthermore, the use of CHO cells results in high product yields, while lymphoid cells are more difficult to culture at an industrial scale. In view of considerable costs for recombinant production of polypeptides and proteins, it is also of utmost importance to maximize the yield of recombinant protein per bioreactor run. Process parameters that have considerable impact on product yield include inter alia the cell culture conditions, the copy number of the nucleic acids (genes) to be expressed, the efficiency with which these genes are transcribed and the corresponding mRNAs are translated, the stability of the mRNA, and the like.

Accordingly, improvements of the strength or transcriptional activity of the regulatory genetic elements controlling gene expression constitute a particularly critical factor in order to augment the yield of recombinant protein produced. Even small incremental increases in transcriptional activity at the single cell level will finally translate into considerable improvements in product yield in high-density industry-scale batch cultures.

The vast majority of mammalian gene expression systems employ expression vectors encoding the heterologous nucleic acid sequences to be expressed under the control of promoter regulatory sequences derived from viruses. Two of the most frequently used viral regulatory elements in these expression cassettes are those of the human cytomegalovirus (hCMV) immediate early genes 1 and 2 (IE1 and IE2). However, a disadvantage associated with the use of hCMV IE1 and IE2 regulatory elements is their pronounced species specificity.

U.S. Pat. No. 5,866,359 discloses that gene expression from such hCMV promoter can be improved by co-expressing adenoviral EIA protein under the control of a weak promoter. EIA is a multifunctional transcription factor which may act on cell cycle regulation and has both independent transcriptional activating and repressing functional domains. Fine tuning of EIA expression is crucial to achieve the ideal balance between gene transactivation and any negative impact on cell cycle progression. However, overexpression of EIA expression could reduce the capacity of the cell to synthesize the recombinant protein of interest.

U.S. Pat. No. 5,591,639 describes vectors comprising, upstream (5') of a heterologous nucleic acid sequence to be expressed, the enhancer, promoter, and complete 5'-untranslated region of the major immediate early gene of the human cytomegalovirus (hCMV-MIE) including intron A (i.e. the first natural intron). However, if the first 400 bp (5'-end) of this sequence (total length of about 2100 bp) were present, poor gene expression rates were observed in both COS7 and CHO cells (Chapman, B. S. et al. (1991) Nucl. Acids Res. 19, 3979-3986).

The transcriptional activity of the regulatory elements of the immediate early genes of the murine cytomegalovirus (mCMV) is higher than that of the hCMV counterparts without exhibiting the pronounced species preference observed for the human sequences (Addison, C. L. et al. (1987) J. Gen. Virol. 78, 1653-1661).

However, attempts to enhance the activity of the mCMV IE promoter regulatory elements, analogously to the hCMV counterparts, by insertion of the natural first intron of the murine major immediate early gene downstream (3') of the mCMV IE promoter failed (cf. inter alia EP patent 1 525 320 81). However, the generation of expression vectors comprising a chimeric cassette composed of the regulatory elements of mCMV IE1 and the natural first intron of the human major immediate early gene resulted in product yields comparable to the use of the fully human sequences (cf., e.g., WO 2006/111387 A2). Similar gene expression rates were also obtained for expression vectors comprising the mCMV IE2 regulatory sequences (cf. inter alia EP patent 1 601 776 81).

Thus, there still remains a need for improved mammalian gene expression systems resulting in high yields of the recombinant polypeptides or proteins produced. In particular, there is a need for mammalian gene expression systems that overcome the above-mentioned limitations, that is, expression systems based on the mCMV or the hCMV promoter sequences but achieving higher expression rates (and thus, product yields) than with the available system Accordingly, it is an object of the present invention to provide such gene expression systems, primarily suitable expression constructs and corresponding mammalian host cells.

SUMMARY OF THE INVENTION

In one aspect, the present invention relates to an expression vector for the heterologous expression of a nucleic acid sequence of interest in mammalian cells, the vector comprising a first chimeric promoter regulatory sequence being operably linked to a first nucleic acid sequence to be expressed, wherein the chimeric promoter regulatory sequence comprises:
(i) a promoter sequence being derived from murine cytomegalovirus or from human cytomegalovirus and being operably linked to the transcriptional start site of the nucleic acid sequence to be expressed; and
(ii) an upstream region and/or enhancer sequence being derived from human and/or simian cytomegalovirus, wherein the upstream region and/or enhancer sequence is located 5' of and operably linked to the murine or the human promoter sequence; and
wherein the chimeric promoter regulatory sequence comprises sequence elements being derived from at least two of the group consisting of murine cytomegalovirus, human cytomegalovirus and simian cytomegalovirus.

In particular embodiments, the promoter sequence is derived from the murine cytomegalovirus IE1 promoter; and/or the upstream region and/or enhancer sequence is derived from the human and/or simian cytomegalovirus IE1 enhancer.

In preferred embodiments, the murine cytomegalovirus IE1 promoter sequence has the nucleotide sequence of SEQ ID NO: 4.

In other particular embodiments, the promoter sequence is derived from the human cytomegalovirus IE1 promoter; and/or the upstream region and/or enhancer sequence is derived from the human and/or simian cytomegalovirus IE1 enhancer.

In preferred embodiments, the human cytomegalovirus IE1 promoter sequence has the nucleotide sequence of SEQ ID NO: 5.

In other preferred embodiments, the upstream region and/or enhancer sequence comprises the nucleotide sequence of SEQ ID NO: 6 being derived from the simian cytomegalovirus IE1 region.

In particularly preferred embodiments, the chimeric promoter regulatory sequence comprises a nucleotide sequence being selected from the group consisting of SEQ ID NO: 7, SEQ ID NO: 8, SEQ ID NO: 9, SEQ ID NO: 10, SEQ ID NO: 11, SEQ ID NO: 12, and SEQ ID NO: 13.

In other particular embodiments, the expression vector further comprises a second chimeric promoter regulatory sequence being operably linked to a second nucleic acid sequence to be expressed, wherein the second chimeric promoter regulatory sequence is identical to the first chimeric promoter regulatory sequence.

In alternative particular embodiments, the expression vector further comprises a second chimeric promoter regulatory sequence being operably linked to a second nucleic acid sequence to be expressed, wherein the second chimeric promoter regulatory sequence is different from the first chimeric promoter regulatory sequence.

Preferably, the first and second nucleic acid sequences to be expressed encode different polypeptides. In specific embodiments, the different polypeptides represent subunits of a dimeric or multimeric protein. Particularly preferably, the dimeric or multimeric protein is an antibody molecule.

In another aspect, the present invention relates to a mammalian host cell transfected with an expression vector as defined herein above. Preferably, the host cell is a CHO cell.

In yet another aspect, the present invention relates to a method for heterologous expression of a nucleic acid sequence of interest in a mammalian host cell, comprising:
(i) transfecting the mammalian host cell with an expression vector as defined herein above; and
(ii) culturing the transfected mammalian host cell under conditions allowing the expression of the nucleic acid sequence of interest.

In preferred embodiments, the transfection is stable transfection.

In a further aspect, the present invention relates to the use of an expression vector as defined herein above for the heterologous expression of a nucleic acid sequence of interest in a mammalian host cell.

Other embodiments of the present invention will become apparent from the detailed description hereinafter.

DETAILED DESCRIPTION OF THE INVENTION

Figure 1:
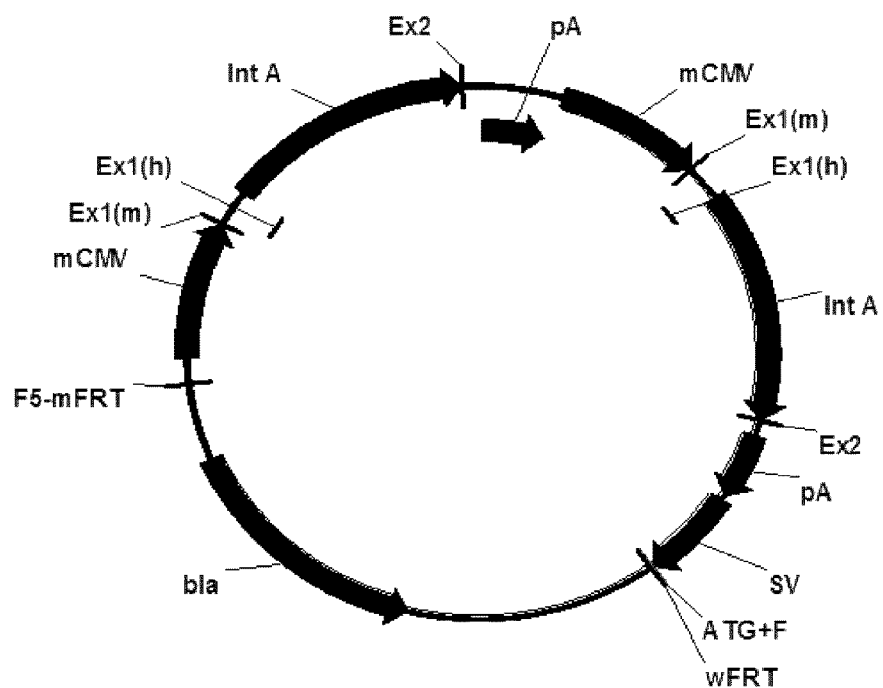
FIG. 1 illustrates expression vector pRY42 (SEQ ID NO: 1) used as "parent vector" for generating the mammalian expression vectors as defined herein. pRY42 encompasses two regulatory cassettes for driving heterologous gene expression (between "mCMV" and "pA", respectively): Multiple cloning sites located 3' (i.e. "downstream") of the "Ex2" regions for insertion of heterologous nucleic acid sequences to be expressed. The regulatory cassettes are flanked by mutant ("F5-mFRT") and wild type ("wFRT") flippase recognition target sites. An in-frame initiation methionine codon has been added to the 5'-end of the wFRT site ("ATG+F") An SV40 early promoter ("SV") is located 5' ("upstream") of ATG+F. Transcription of heterologous nucleic acid sequences is driven by the promoter of the murine cytomegalovirus IE1 gene ("mCMV") which is followed by the 5'UTR, where exon 1 ("Ex1") is a hybrid of murine ("m") and human ("h") CMV derived sequences, and where exon 2 ("Ex2") and the intron A sequence ("Int A") are derived from the hCMV sequence. The 13-lactamase selection marker gene is denoted as "bla". pRY42 is used as a target vector for cloning the different chimeric promoter regulatory sequences as defined herein.

The present invention is based on the unexpected finding that mammalian expression vectors comprising chimeric (i.e. hybrid) promoter regulatory sequences being composed of a mCMV or a hCMV promoter sequence (in particular, a mCMV or a hCMV IE1 promoter sequence) in operable linkage to the transcriptional start site of the nucleic acid sequence to be expressed and an hCMV and/or sCMV upstream region and/or enhancer sequence (in particular, a hCMV IE1 and/or sCMV IE1 enhancer sequence) being located 5' of and operably linked to the mCMV or the hCMV promoter sequence resulted in significantly improved gene expression rates as compared to existing expression systems only based on mCMV promoter sequences, and thus also in much higher yields (up to an almost 3-fold increase) of the recombinant proteins produced.

Accordingly, the mammalian expression vectors as defined herein represent superior molecular tools for the production of recombinant proteins, particularly in an industry-scale.

The present invention illustratively described in the following may suitably be practiced in the absence of any element or elements, limitation or limitations, not specifically disclosed herein.

Where the term "comprising" is used in the present description and the claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun, e.g., "a", "an" or "the", this includes a plural of that noun unless specifically stated otherwise.

In case, numerical values are indicated in the context of the present invention the skilled person will understand that the technical effect of the feature in question is ensured within an interval of accuracy, which typically encompasses a deviation of the numerical value given of ±10%, and preferably of ±5%.

Furthermore, the terms first, second, third, (a), (b), (c), and the like, in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used. The following terms or definitions are provided solely to aid in the understanding of the invention. These definitions should not be construed to have a scope less than understood by a person of ordinary skill in the art.

In one aspect, the present invention relates to an expression vector for the heterologous expression of a nucleic acid sequence of interest in mammalian cells, the vector comprising a first chimeric promoter regulatory sequence being operably linked to a first nucleic acid sequence to be expressed, wherein the chimeric promoter regulatory sequence comprises:

(i) a promoter sequence being derived from murine cytomegalovirus or from human cytomegalovirus and being operably linked to the transcriptional start site of the nucleic acid sequence to be expressed; and (ii) an upstream region and/or enhancer sequence being derived from human and/or simian cytomegalovirus, wherein the upstream region and/or enhancer sequence is located 5' of and operably linked to the murine or the human promoter sequence, and wherein the chimeric promoter regulatory sequence comprises sequence elements being derived from at least two of the group consisting of murine cytomegalovirus, human cytomegalovirus and simian cytomegalovirus.

In other words, the provision that the chimeric promoter regulatory sequence, as defined herein, comprises sequence elements being derived from at least two of the group consisting of murine cytomegalovirus, human cytomegalovirus and simian cytomegalovirus ensures that the claimed subject matter does not include any constructs only derived from human cytomegalovirus.

The term "expression vector", as used herein, denotes a nucleic acid vehicle (plasmid) that is characterized by the presence of at least one "expression cassette". The term "expression cassette", as used herein, refers to a genetic construct that is capable to allow gene expression of a nucleic acid sequence of interest (i.e. a "heterologous" nucleic acid sequence). This requires that such expression cassette comprises regulatory sequence elements which contain information regarding to transcriptional and/or translational regulation, and that such regulatory sequences are "operably linked" to the nucleic acid sequence of interest. An operable linkage is a linkage in which the regulatory sequence elements and the nucleic acid sequence to be expressed are connected in a way that enables gene expression.

The precise nature of the regulatory regions of an "expression cassette" that are necessary for controlling and driving gene expression may vary among species, but in general these regions comprise promoter regulatory sequences (i.e. a sequence region located 5' ("upstream") of the nucleic acid sequence of interest) and 3'-untranslated regulatory sequences (i.e. a sequence region located 3' ("downstream") of the nucleic acid sequence of interest).

The term "promoter", (also referred to as "core promoter") as used herein, denotes sequence elements that per se direct the initiation of transcription (e.g., binding sites for transcription factors and for DNA-dependent RNA-polymerase, TATA box, CAAT sequences, and 5'-capping elements). As long as this functionality of promoting transcription initiation is retained or substantially retained (e.g., at least 70%, at least 80%, at least 90% or at least 95% of wild-type activity, that is, activity of a full-length sequence), any truncated, mutated or otherwise modified variants of a (naturally occurring) wild-type promoter sequence are also within the above definition. As used herein, the term "core promoter" refers to a sequence of minimal length that retains promoter activity. As used herein, the promoter sequence is operably linked to the transcriptional start site of the nucleic acid sequence to be expressed.

In particular embodiments, the expression vectors of the present invention comprise (as part of an expression cassette) a first (chimeric) promoter regulatory sequence (i.e. at least one such sequence), which, in turn, encompasses a (core) promoter sequence being derived from murine cytomegalovirus (mCMV). This mCMV promoter sequence is operably linked to the transcriptional start site of a first nucleic acid sequence to be expressed. Generally, any mCMV promoter sequence can be employed. Preferably, promoter sequences of the mCMV immediate early (IE) genes, such as mCMV IE1 and mCMV IE2 (Dorsch-Hasler, K. et al. (1985) *Proc. Natl. Acad. Sci. USA* 82, 8325-8329; Messerle, M. et al. (1991) *J. Virol.* 65, 1638-1643), are employed, with the mCMV IE1 promoter being particularly preferred.

These and additional mCMV promoters are well known in the art and can be easily derived from the mCMV genome deposited in the NCBI Viral Genomes database under accession no. U68299.1 (http://www.ncbi.nlm.nih.gov/genomes/GenomesHome; Bao, Y. et al. (2004) *J. Virol.* 78, 7291-7298).

In a specific embodiment of the present invention, the mCMV IE1 promoter sequence comprised in the expression vector has a nucleic acid sequence of 492 bp in length as shown in SEQ ID NO: 3:

```
  1 tactgagtca ttagggactt tccaatgggt tttgcccagt acataaggtc
 51 aatagggtg aatcaacagg aaagtcccat tggagccaag tacactgagt
101 caatagggac tttccattgg gttttgccca gtacaaaagg tcaatagggg
151 gtgagtcaat gggttttttcc cattattggc acgtacataa ggtcaatagg
201 ggtgagtcat tgggttttttc cagccaattt aattaaaacg ccatgtactt
251 tcccaccatt gacgtcaatg ggctattgaa actaatgcaa cgtgaccttt
301 aaacggtact ttcccatagc tgattaatgg gaaagtaccg ttctcgagcc
351 aatacacgtc aatgggaagt gaaagggcag ccaaaacgta acaccgcccc
401 ggttttcccc tggaaattcc atattggcac gcattctatt ggctgagctg
451 cgttctacgt gggtataaga ggcgcgacca gcgtcggtac cg
```

In a preferred embodiment, the mCMV IE1 promoter sequence comprised in the expression vector has a nucleic acid sequence of 102 bp in length (also referred to as "core promoter") as shown in SEQ ID NO: 4:

```
  1 acaccgcccc ggttttcccc tggaaattcc atattggcac gcattctatt
 51 ggctgagctg cgttctacgt gggtataaga ggcgcgacca gcgtcggtac
101 cg
```

Both SEQ ID NO: 3 and SEQ ID NO: 4 include at their respective 3'-ends an additional guanosine ("G") nucleotide, which represents the transcriptional start site.

In other particular embodiments, the expression vectors of the present invention comprise (as part of an expression cassette) a first (chimeric) promoter regulatory sequence (i.e. at least one such sequence), which, in turn, encompasses a (core) promoter sequence being derived from human cytomegalovirus (hCMV). This hCMV promoter sequence is operably linked to the transcriptional start site of a first nucleic acid sequence to be expressed. Generally, any hCMV promoter sequence can be employed. Preferably, promoter sequences of the hCMV immediate early (IE) genes, such as hCMV IE1 and hCMV IE2 (You, C. Y. et al. (1992) *Intervirology* 34, 94-104; Klucher, K. M. et al. (1993) *Mol. Cell. Biol.* 13, 1238-1250), are employed, with the hCMV IE1 promoter being particularly preferred.

These and additional hCMV promoters are well known in the art and can be easily derived from the hCMV genome deposited in the NCBI Viral Genomes database under accession no. NC_006273 (http://www.ncbi.nlm.nih.gov/genomes/GenomesHome; supra).

In a preferred embodiment, the hCMV IE1 promoter sequence comprised in the expression vector has a nucleic acid sequence of 117 bp in length (also referred to as "core promoter") as shown in SEQ ID NO: 5:

```
  1 gcaccaaaat caacgggact ttccaaaatg tcgtaacaac tccgccccat
 51 tgacgcaaat gggcggtagg cgtgtacggt gggaggtcta tataagcaga
101 gctcgtttag tgaaccg
```

SEQ ID NO: 5 includes at its 3'-end an additional guanosine ("G") nucleotide, which represents the transcriptional start site.

Furthermore, the promoter regulatory sequences of an expression cassette usually comprise an "enhancer" sequence. The term "enhancer", as used herein, denotes sequence elements that augment, improve or ameliorate transcription of a nucleic acid sequence irrespective of its location and orientation in relation to the nucleic acid sequence to be expressed. An enhancer may enhance transcription from a single promoter or simultaneously from more than one promoter. As long as this functionality of improving transcription is retained or substantially retained (e.g., at least 70%, at least 80%, at least 90% or at least 95% of wild-type activity, that is, activity of a full-length sequence), any truncated, mutated or otherwise modified variants of a (naturally occurring) wild-type enhancer sequence are also within the above definition.

The expression vectors of the present invention comprise (as part of an expression cassette) in their respective first (chimeric) promoter regulatory sequence an upstream region (sequence) and/or enhancer sequence being derived from human cytomegalovirus (hCMV) and/or simian cytomegalovirus (sCMV). In other words, the promoter regulatory sequence may comprise an upstream region and/or enhancer sequence being solely derived from hCMV or an upstream region and/or enhancer sequence being solely derived from sCMV or a chimeric upstream region and/or enhancer sequence composed of sequences derived from hCMV and sCMV. Within the promoter regulatory sequence, the upstream region and/or enhancer sequences are located 5' (i.e. "upstream") of the mCMV or the hCMV (core) promoter sequences and are in operable linkage to the murine or the human promoter sequence. Typically, the enhancer sequences are arranged in the same orientation as the promoter sequences. However, in specific embodiments, the upstream region and/or enhancer sequences are arranged in reverse orientation in relation to the promoter sequences.

Generally, any hCMV and/or sCMV sequences can be employed as upstream region and/or enhancer sequence. Preferably, sequences of the hCMV and/or sCMV immediate early (IE) genes, such as hCMV IE1, hCMV IE2, sCMV IE1, and sCMV IE2 (Meier, J. L. and Stinski, M. F. (1996) *Intervirology* 39, 331-342; Kim, G. Y. et al. (2011) *Biotechnol. Lett.* 33, 1319-1326), are employed, with the hCMV and/or sCMV IE1 enhancer sequences being particularly preferred.

Hence, the expression vectors of the present invention comprise a first promoter regulatory sequence which is chimeric in that it comprises mCMV promoter sequences or hCMV promoter sequences in combination with hCMV and/or sCMV upstream region and/or enhancer sequences. In particular embodiments, the promoter sequence is derived from the mCMV IE1 promoter; and/or the upstream region and/or enhancer sequence is derived from the hCMV and/or sCMV IE1 enhancer. In other particular embodiments, the promoter sequence is derived from the mCMV IE1 promoter; and/or the upstream region and/or enhancer sequence is derived from the hCMV and/or sCMV IE2 enhancer. In yet other particular embodiments, the promoter sequence is derived from the hCMV IE1 promoter; and/or the upstream region and/or enhancer sequence is derived from the hCMV and/or sCMV IE1 enhancer. In yet other particular embodiments, the promoter sequence is derived from the hCMV IE2 promoter; and/or the upstream region and/or enhancer sequence is derived from the hCMV and/or sCMV IE2 enhancer.

These and additional hCMV and/or sCMV sequences are well known in the art and can be easily derived from the hCMV and sCMV genomes deposited in the NCBI Viral Genomes database under accession nos. X17403.1 and U38308.1, respectively.

In further preferred embodiments, the sequence of the upstream region comprises the nucleotide sequence of 452 bp in length, as shown in SEQ ID NO: 6, being derived from the sCMV IE1 enhancer region.

```
  1 gaccatagcc aattcaatat ggcgtatatg gactcatgcc aattcaatat
 51 ggtggatctg gacctgtgcc aattcaatat ggcgtatatg gactcgtgcc
101 aattcaatat ggtggatctg gacccccagcc aattcaatat ggcggacttg
151 gcaccatgcc aattcaatat ggcggacctg gcactgtgcc aactggggag
201 gggtctactt ggcacggtgc caagtttgag gaggggtctt ggccctgtgc
251 caagtccgcc atattgaatt ggcatggtgc caataatggc ggccatattg
301 gctatatgcc aggatcaata tataggcaat atccaatatg gccctatgcc
351 aatatggcta ttggccaggt tcaatactat gtattggccc tatgccatat
401 agtattccat atatgggttt tcctattgac gtagatagcc cctcccaatg
451 gg
```

In some of these preferred embodiments, the nucleic acid sequence of SEQ ID NO: 6 is an integral part of a longer sequence element being derived from the sCMV IE1 region (cf., e.g., SEQ ID NO: 11). In some other of these preferred embodiments, the sequence element being derived from the sCMV IE1 region has the sequence of SEQ ID NO: 6, which is present in combination with a further sequence element being derived from the hCMV IE1 region (cf., e.g., SEQ ID NO: 10).

In particularly preferred embodiments, the chimeric promoter regulatory sequence comprises a nucleotide sequence being selected from the group consisting of SEQ ID NO: 7, SEQ ID NO: 8, SEQ ID NO: 9, SEQ ID NO: 10, SEQ ID NO: 11, SEQ ID NO: 12, and SEQ ID NO: 13.

The chimeric promoter regulatory sequence according to SEQ ID NO: 7 (herein also referred to as "construct 1") has a total length of 1074 bp and is composed of a 582 bp hCMV IE1 upstream and mCMV IE1 enhancer sequence (shown in italics) and a 492 bp mCMV IE1 promoter sequence (also shown as SEQ ID NO: 3).

```
   1 ctgcagtgaa taataaaatg tgtgtttgtc cgaaatacgc gttttgagat
  51 ttctgtcgcc gactaaattc atgtcgcgcg atagtggtgt ttatcgccga
 101 tagagatggc gatattggaa aaatcgatat ttgaaaatat ggcatattga
 151 aaatgtcgcc gatgtgagtt tctgtgtaac tgatatcgcc attttccaa
 201 aagtgatttt tggcatacg cgatatctgg cgatagcgct tatatcgttt
 251 acggggatg gcgatagacg actttggtga cttgggcgat tctgtgtgtc
 301 gcaaatatcg cagtttcgat ataggtgaca gacgatatga ggctatatcg
 351 ccgatagagg cgacatcaag ctggcacatg gccaatgcat atcgatctat
 401 acattgaatc aatattggcc attagccata ttattcattg gttatatagc
 451 ataaatcaat attggctatt ggccattgca tacgttgtat ccatatcata
 501 atatgtacat ttatattggc tcatgtccaa cattaccgcc atgttgacat
 551 tgattattga ctagttatta atagtaatca attactgagt cattagggac
 601 tttccaatgg gttttgccca gtacataagg tcaataggg tgaatcaaca
 651 ggaaagtccc attggagcca agtacactga gtcaataggg actttccatt
 701 gggttttgcc cagtacaaaa ggtcaatagg gggtgagtca atgggtttt
 751 cccattattg gcacgtacat aaggtcaata ggggtgagtc attgggtttt
 801 tccagccaat ttaattaaaa cgccatgtac tttcccacca ttgacgtcaa
 851 tgggctattg aaactaatgc aacgtgacct ttaaacggta ctttcccata
 901 gctgattaat gggaaagtac cgttctcgag ccaatacacg tcaatgggaa
 951 gtgaaagggc agccaaaacg taacaccgcc ccggttttcc cctggaaatt
1001 ccatattggc acgcattcta ttggctgagc tgcgttctac gtgggtataa
1051 gaggcgcgac cagcgtcggt accg
```

The chimeric promoter regulatory sequence according to SEQ ID NO: 8 (herein also referred to as "construct 2") has a total length of 1128 pb and is composed of a 1026 bp sequence including the hCMV IE1 upstream sequence and the hCMV IE1 enhancer sequence (shown in italics) and a 102 bp mCMV IE1 "core" promoter sequence (also shown as SEQ ID NO: 4).

```
   1 ctgcagtgaa taataaaatg tgtgtttgtc cgaaatacgc gttttgagat
  51 ttctgtcgcc gactaaattc atgtcgcgcg atagtggtgt ttatcgccga
 101 tagagatggc gatattggaa aaatcgatat ttgaaaatat ggcatattga
 151 aaatgtcgcc gatgtgagtt tctgtgtaac tgatatcgcc attttccaa
 201 aagtgatttt tggcatacg cgatatctgg cgatagcgct tatatcgttt
 251 acggggatg gcgatagacg actttggtga cttgggcgat tctgtgtgtc
```

```
301 gcaaatatcg cagtttcgat ataggtgaca gacgatatga ggctatatcg 351 ccgatagagg cgacatcaag ctggcacatg gccaatgcat atcgatctat 401 acattgaatc aatattggcc attagccata ttattcattg gttatatagc 451 ataaatcaat attggctatt ggccattgca tacgttgtat ccatatcata 501 atatgtacat ttatattggc tcatgtccaa cattaccgcc atgttgacat 551 tgattattga ctagttatta atagtaatca attacggggt cattagttca 601 tagcccatat atggagttcc gcgttacata acttacggta aatggcccgc 651 ctggctgacc gcccaacgac ccccgcccat tgacgtcaat aatgacgtat 701 gttcccatag taacgccaat agggactttc cattgacgtc aatgggtgga 751 gtatttacgg taaactgccc acttggcagt acatcaagtg tatcatatgc 801 caagtacgcc ccctattgac gtcaatgacg gtaaatggcc cgcctggcat 851 tatgcccagt acatgacctt atgggacttt cctacttggc agtacatcta 901 cgtattagtc atcgctatta ccatggtgat gcggttttgg cagtacatca 951 atgggcgtgg atagcggttt gactcacggg gatttccaag tctccacccc 1001 attgacgtca atgggagttt gttttgacac cgccccggtt ttcccctgga 1051 aattccatat tggcacgcat tctattggct gagctgcgtt ctacgtgggt 1101 ataagaggcg cgaccagcgt cggtaccg
```

The chimeric promoter regulatory sequence according to SEQ ID NO: 9 (herein also referred to as "construct 3") has a total length of 509 pb and is composed of a 407 bp hCMV IE1 enhancer sequence (shown in italics) and a 102 bp mCMV IE1 "core" promoter sequence (also shown as SEQ ID NO: 4).

```
  1 cgcgttacat aacttacggt aaatggcccg cctggctgac cgcccaacga 51 ccccgccca ttgacgtcaa taatgacgta tgttcccata gtaacgccaa 101 tagggacttt ccattgacgt caatgggtgg agtatttacg gtaaactgcc 151 cacttggcag tacatcaagt gtatcatatg ccaagtacgc ccctattga 201 cgtcaatgac ggtaaatggc ccgcctggca ttatgcccag tacatgacct 251 tatgggactt tcctacttgg cagtacatct acgtattagt catcgctatt 301 accatggtga tgcggttttg gcagtacatc aatgggcgtg gatagcggtt 351 tgactcacgg ggatttccaa gtctccaccc cattgacgtc aatgggagtt 401 tgttttgaca ccgccccggt tttcccctgg aaattccata ttggcacgca 451 ttctattggc tgagctgcgt tctacgtggg tataagaggc gcgaccagcg 501 tcggtaccg
```

The chimeric promoter regulatory sequence according to SEQ ID NO: 10 (herein also referred to as "construct 4") has a total length of 961 pb and is composed of a 452 bp sCMV IE1 upstream sequence (shown in bold; SEQ ID NO: 6), a 407 bp hCMV IE1 enhancer sequence (shown in italics) and a 102 bp mCMV IE1 "core" promoter sequence (also shown as SEQ ID NO: 4).

```
  1 gaccatagcc aattcaatat ggcgtatatg gactcatgcc aattcaatat 51 ggtggatctg gacctgtgcc aattcaatat ggcgtatatg gactcgtgcc 101 aattcaatat ggtggatctg gaccccagcc aattcaatat ggcggacttg
```

```
151 gcaccatgcc aattcaatat ggcggacctg gcactgtgcc aactggggag 201 gggtctactt ggcacggtgc caagtttgag gagggtctt ggccctgtgc 251 caagtccgcc atattgaatt ggcatggtgc caataatggc ggccatattg 301 gctatatgcc aggatcaata taggcaat atccaatatg gccctatgcc 351 aatatggcta ttggccaggt tcaatactat gtattggccc tatgccatat 401 agtattccat atatgggttt tcctattgac gtagatagcc cctcccaatg 451 ggcgcgttac ataacttacg gtaaatggcc cgcctggctg accgcccaac 501 gaccccgcc cattgacgtc aataatgacg tatgttccca tagtaacgcc 551 aatagggact ttccattgac gtcaatgggt ggagtattta cggtaaactg 601 cccacttggc agtacatcaa gtgtatcata tgccaagtac gccccctatt 651 gacgtcaatg acggtaaatg gcccgcctgg cattatgccc agtacatgac 701 cttatgggac tttcctactt ggcagtacat ctacgtatta gtcatcgcta 751 ttaccatggt gatgcggttt tggcagtaca tcaatgggcg tggatagcgg 801 tttgactcac ggggatttcc aagtctccac cccattgacg tcaatgggag 851 tttgttttga caccgcccg gttttcccct ggaaattcca tattggcacg 901 cattctattg gctgagctgc gttctacgtg ggtataagag gcgcgaccag 951 cgtcggtacc g
```

The chimeric promoter regulatory sequence according to SEQ ID NO: 11 (herein also referred to as "construct 5") has a total length of 909 bp and is composed of a 807 bp sequence including elements of the sCMV IE1 upstream region and the sCMV IE1 enhancer sequence (shown in bold; SEQ ID NO: 6 being underlined) and a 102 bp mCMV IE1 "core" promoter sequence (shown as SEQ ID NO: 4).

```
  1 gaccatagcc aattcaatat ggcgtatatg gactcatgcc aattcaatat 51 ggtggatctg gacctgtgcc aattcaatat ggcgtatatg gactcgtgcc 101 aattcaatat ggtggatctg gaccccagcc aattcaatat ggcggacttg 151 gcaccatgcc aattcaatat ggcggacctg gcactgtgcc aactggggag 201 gggtctactt ggcacggtgc caagtttgag gagggtctt ggccctgtgc 251 caagtccgcc atattgaatt ggcatggtgc caataatggc ggccatattg 301 gctatatgcc aggatcaata taggcaat atccaatatg gccctatgcc 351 aatatggcta ttggccaggt tcaatactat gtattggccc tatgccatat 401 agtattccat atatgggttt tcctattgac gtagatagcc cctcccaatg 451 ggcggtccca tataccatat atggggcttc ctaataccgc ccatagccac 501 tcccccattg acgtcaatgg tctctatata tggtctttcc tattgacgtc 551 atatgggcgg tcctattgac gtatatggcg cctcccccat tgacgtcaat 601 tacggtaaat ggcccgcctg gctcaatgcc cattgacgtc aataggacca 651 cccaccattg acgtcaatgg gatggctcat tgcccattca tatccgttct 701 cacgccccct attgacgtca atgacggtaa atgcccact tggcagtaca 751 tcaatatcta ttaatagtaa cttggcaagt acattactat tggaagtacg 801 ccagggtaca ccgccccggt ttttcccctgg aaattccata ttggcacgca 851 ttctattggc tgagctgcgt tctacgtggg tataagaggc gcgaccagcg 901 tcggtaccg
```

The chimeric promoter regulatory sequence according to SEQ ID NO: 12 (herein also referred to as "construct 6") has a total length of 976 bp and is composed of a 452 bp sCMV IE1 upstream region (shown in bold), a 407 bp hCMV IE1 enhancer sequence (shown in italics), and a 117 bp hCMV "core" promoter sequence (shown as SEQ ID NO: 5).

```
  1 gaccatagcc aattcaatat ggcgtatatg gactcatgcc aattcaatat
 51 ggtggatctg gacctgtgcc aattcaatat ggcgtatatg gactcgtgcc
101 aattcaatat ggtggatctg gaccccagcc aattcaatat ggcggacttg
151 gcaccatgcc aattcaatat ggcggacctg gcactgtgcc aactggggag
201 gggtctactt ggcacggtgc caagtttgag gagggggtctt ggccctgtgc
251 caagtccgcc atattgaatt ggcatggtgc caataatggc ggccatattg
301 gctatatgcc aggatcaata tataggcaat atccaatatg gcctatgcc
351 aatatggcta ttggccaggt tcaatactat gtattggccc tatgccatat
401 agtattccat atatgggttt tcctattgac gtagatagcc cctcccaatg
451 ggcgcgttac ataacttacg gtaaatggcc cgcctggctg accgcccaac
501 gacccccgcc cattgacgtc aataatgacg tatgttccca tagtaacgcc
551 aatagggact ttccattgac gtcaatgggt ggagtattta cggtaaactg
601 cccacttggc agtacatcaa gtgtatcata tgccaagtac gccccctatt
651 gacgtcaatg acggtaaatg gcccgcctgg cattatgccc agtacatgac
701 cttatgggac tttcctactt ggcagtacat ctacgtatta gtcatcgcta
751 ttaccatggt gatgcggttt tggcagtaca tcaatgggcg tggatagcgg
801 tttgactcac ggggatttcc aagtctccac cccattgacg tcaatgggag
851 tttgttttgg caccaaaatc aacgggactt tccaaaatgt cgtaacaact
901 ccgccccatt gacgcaaatg ggcggtaggc gtgtacggtg ggaggtctat
951 ataagcagag ctcgtttagt gaaccg
```

The chimeric promoter regulatory sequence according to SEQ ID NO: 13 (herein also referred to as "construct 7") has a total length of 924 bp and is composed of a 807 bp sCMV IE1 upstream region and enhancer sequence (shown in bold; the portion also included in "construct 4" being underlined) and a 117 bp hCMV "core" promoter (shown as SEQ ID NO: 5).

```
  1 gaccatagcc aattcaatat ggcgtatatg gactcatgcc aattcaatat
 51 ggtggatctg gacctgtgcc aattcaatat ggcgtatatg gactcgtgcc
101 aattcaatat ggtggatctg gaccccagcc aattcaatat ggcggacttg
151 gcaccatgcc aattcaatat ggcggacctg gcactgtgcc aactggggag
201 gggtctactt ggcacggtgc caagtttgag gagggggtctt ggccctgc
251 caagtccgcc atattgaatt ggcatggtgc caataatggc ggccatattg
301 gctatatgcc aggatcaata tataggcaat atccaatatg gcctatgcc
351 aatatggcta ttggccaggt tcaatactat gtattggccc tatgccatat
401 agtattccat atatgggttt tcctattgac gtagatagcc cctcccaatg
451 ggcggtccca tataccatat atgggggcttc ctaataccgc ccatagccac
501 tcccccattg acgtcaatgg tctctatata tggtctttcc tattgacgtc
551 atatgggcgg tcctattgac gtatatgcgc cctcccccat tgacgtcaat
601 tacggtaaat ggcccgcctg gctcaatgcc cattgacgtc ataggacca
```

```
651 cccaccattg acgtcaatgg gatggctcat tgcccattca tatccgttct 701 cacgccccct attgacgtca atgacggtaa atggcccact tggcagtaca 751 tcaatatcta ttaatagtaa cttggcaagt acattactat tggaagtacg 801 ccagggtgca ccaaaatcaa cgggactttc caaaatgtcg taacaactcc 851 gccccattga cgcaaatggg cggtaggcgt gtacggtggg aggtctatat 901 aagcagagct cgtttagtga accg
```

In specific embodiments, the chimeric promoter regulatory sequence is composed of a hCMV and/or sCMV IE2 upstream region and/or enhancer sequence and a mCMV IE2 promoter sequence. In other specific embodiments, the chimeric promoter regulatory sequence is composed of a hCMV and/or sCMV IE2 upstream region and/or enhancer sequence and a hCMV IE2 promoter sequence In yet other specific embodiments, the chimeric promoter regulatory sequence is composed of a hCMV and/or sCMV IE1 upstream region and/or enhancer sequence and a mCMV IE2 promoter sequence. In yet other specific embodiments, the chimeric promoter regulatory sequence is composed of a hCMV and/or sCMV IE1 upstream region and/or enhancer sequence and a hCMV IE2 promoter sequence. In yet other specific embodiments, the chimeric promoter regulatory sequence is composed of a hCMV and/or sCMV IE2 upstream region and/or enhancer sequence and a mCMV IE1 promoter sequence. In yet other specific embodiments, the chimeric promoter regulatory sequence is composed of a hCMV and/or sCMV IE2 upstream region and/or enhancer sequence and a hCMV IE1 promoter sequence.

The 3'-regulatory sequences of an "expression cassette" as defined herein typically encompass regulatory elements involved in transcriptional termination, polyadenylation, or the like. If, however, these termination sequences are not satisfactory functional in a particular host cell, then they may be substituted with signals functional in that cell.

Further regulatory elements comprised in such an "expression cassette" include inter alia internal ribosome entry sites (IRES; allowing for the expression of "polycistronic" nucleic acid sequences) as well as translated signal sequences for targeting the native polypeptide to a specific compartment of a host cell. Exemplary signal sequences suitable for CHO cells are disclosed, for example, in WO 2008/148519 A2. The skilled person is also well aware of all these regulatory elements and how to select such elements suitable for the expression of a nucleic acid sequence in a particular cellular setting.

The expression vector of the present invention may be, e.g., a plasmid, cosmid, phagemid, artificial chromosome, or another vehicle commonly used in genetic engineering.

Such expression vectors typically include, aside from one or more "expression cassettes" encompassing the regulatory sequences described above, one or more multiple cloning sites in order to facilitate insertion and/or removal of nucleic acid sequences. The multiple cloning sites may be located upstream and downstream of the expression cassettes described above, thus allowing replacement of the entire cassette. Multiple cloning sites may also be located within such an expression cassette downstream of the promoter regulatory sequences and upstream of the 3'-regulatory sequences, thus allowing insertion or replacement of a nucleic acid sequence to be expressed. For stable transfections (cf. below), the expression vectors may further comprise recognition sequences for site-specific integrases or recombinases in order to facilitate recombination and stable integration in the genome of the host cell.

In addition, the expression vectors as defined herein typically comprise at least one origin of replication as well as control sequences derived from a species compatible with the host cell employed in order to ensure autonomous replication/episomal maintenance of the expression vector (in particular, for use in transient transfections; cf. below). Exemplary origins of replication in mammalian include the SV40 or and the EBV origin of replication. Specifically designed expression vectors (i.e. shuttle vectors) comprising more than one origin of replication allow the shuttling between different hosts, such as between bacterial and animal cells. Suitable origins of replication for prokaryotic cells include, for example, the ColE1 and M13 origins of replication.

Furthermore, an expression vector as defined herein may comprise one or more selection markers conferring a selectable phenotype on transfected cells. Suitable selection markers include inter alia the hygromycin B phosphatase gene, the thymidine kinase gene, the ornithine decarboxylase gene, the dihydrofolate reductase gene, and the glutamine synthase gene. Preferably, the glutamine synthase (GS) gene is employed (Cockett, D. K. et al. (1990) Bio/Technology 8, 662-667; Bebbington, C. R. et al. (1992) Bio/Technology 10:169-175;).

Numerous methods that can be used to design and/or modify recombinant expression vectors are well established in the art (see, e.g., Sambrook, J., and Russel, D. W. (2001), Molecular cloning: A laboratory manual (3rd Ed.) Cold Spring Harbor, N.Y., Cold Spring Harbor Laboratory Press; Ausubel, F. M. et al. (2001) Current Protocols in Molecular Biology, Wiley & Sons, Hoboken, N.J., USA). Large numbers of suitable mammalian expression vectors are also commercially available and well known to the skilled person who is also able to determine which vectors are suitable for expressing a nucleic acid molecule of interest in a given setting. Examples of such vectors include inter alia pcDNA3, pFRT, pTARGET, pSV2-dhfr as well as derivatives of the vectors pRY42 (SEQ ID NO: 1) and pRY57 (SEQ ID NO: 2) described herein below.

The nucleic acid sequences to be expressed by employing the expression vectors of the invention may be monocistronic (i.e. encode a single polypeptide or protein including fusion proteins) or polycistronic (i.e. encode two or more individual polypeptides or proteins).

In particular embodiments, the expression vector comprises a single (i.e. first) chimeric promoter regulatory sequence being operably linked to a (first) nucleic acid sequence to be expressed, In other particular embodiments, the expression vector further comprises a second chimeric promoter regulatory sequence being operably linked to a second nucleic acid sequence to be expressed, wherein the second chimeric promoter regulatory sequence is identical to the first chimeric promoter regulatory sequence. For example, the first and second chimeric promoter regulatory sequences are composed of an hCMV/sCMV IE1 upstream region and/or enhancer sequence in combination with a mCMV IE1 or hCMV IE1 promoter sequence.

In alternative particular embodiments, the expression vector further comprises a second chimeric promoter regulatory sequence being operably linked to a second nucleic acid sequence to be expressed, wherein the second chimeric promoter regulatory sequence is different from the first chimeric promoter regulatory sequence. For example, the first chimeric promoter regulatory sequence is composed of an hCMV and/or sCMV IE2 upstream region and/or enhancer sequence and a mCMV IE2 or a hCMV IE2 promoter sequence, whereas the second chimeric promoter regulatory sequence is composed of an hCMV and/or sCMV IE1 upstream region and/or enhancer sequence and a mCMV IE1 or a hCMV IE1 promoter sequence.

In specific embodiments, the expression vector comprises a third chimeric promoter regulatory sequence being operably linked to a third nucleic acid sequence to be expressed, wherein the third chimeric promoter regulatory sequence may be identical to the first and/or second promoter regulatory sequence or may be different from both the first and second chimeric promoter regulatory sequences. In further specific embodiments, the expression vector comprises more than three chimeric promoter regulatory sequences.

The nucleic acid sequences to be expressed by employing the expression vectors of the present invention may encode any polypeptides or proteins of interest, in particular polypeptides or proteins having diagnostic or therapeutic applicability, such as inter alia growth factors, cytokines (interferons, interleukins), hormones, tyrosine kinases, receptors (GPCRs), integrins, transcription factors, blood clotting factors, single-chain antibodies, antibody fragments or antibody-like molecules (anticalins), and the like.

In case of expression vectors as defined herein comprising two chimeric promoter regulatory sequences (as part of expression cassettes), the first and second nucleic acid sequences to be expressed encode different polypeptides (or proteins). In specific embodiments, the different polypeptides represent subunits of a dimeric or multimeric protein, such as inter alia homomeric or heteromeric receptor molecules, peptide hormones, DNA/RNA polymerases, hemoglobins, vaccines, and the like.

In particularly preferable embodiments, the dimeric or multimeric protein is a "classical" antibody molecule comprising the light chain as the first subunit and the heavy chain as the second subunit. The antibody molecule may be a naturally occurring or a genetically engineered antibody, either a full-length antibody or a truncated variant thereof (such as Fab' fragments, Fab' fragments, $F(ab')_2$ fragments). IgG immunoglobulin antibodies are particularly preferred. Depending on the specific application, the antibody molecules may be chimeric (e.g., murine/human), humanized or fully human.

In other embodiments employing expression vectors comprising two chimeric promoter regulatory sequences, the first and second nucleic acid sequence to be expressed encode a "target protein" to be analyzed and a corresponding reporter protein (such as green fluorescent protein, luciferase, alkaline phosphatase, β-galactosidase, and horseradish peroxidase) for monitoring, e.g., cellular localization or functional activity of the target protein.

When using two (or more) chimeric promoter regulatory sequences exhibiting different rates of gene expression it may be possible to produce certain molar ratios of the corresponding proteins of interest.

In another aspect, the present invention relates to a mammalian host cell transfected with an expression vector as defined herein above.

Suitable host cells include any type of mammalian cells, the cells being of human or non-human origin. Mammalian cells of non-human origin include inter alia cells derived from mouse, rat, hamster, rabbit, cat, dog, pig, cow, horse or monkey.

Suitable mammalian host cells include immortalized cell lines such as human Hela, MRC5 fibroblasts, 983M melanoma, HEK293, H9, MCF7, and Jurkat cells; MOCK canine kidney cells; RF cultured rat lung fibroblasts isolated from Sprague-Dawley rats; murine NIH3T3, C127, P815 mastocytoma, MT1A2 mammary adenocarcinoma, and L cells; simian COS1 and COS? cells, quail QC1-3 cells; and Chinese hamster ovary (CHO) cells or cell lines.

In preferred embodiments, the host cells employed are CHO cells or CHO cell lines.

Suitable CHO cell lines include inter alia CHO KI (Tjio, J. T. and Puck, T. T. (1958) *J. Exp. Med.* 108, 945-955), CHO pro3-, CHO DG44, CHO P12, dhfr-negative DUK-811 (Urlaub, G. and Chasin L. A. (1980) *Proc. Natl. Acad. Sci. USA* 77, 4216-4220), and particularly CHOK1SV (Lonza Ltd. Basel, Switzerland). CHOK1SV is a suspension, protein-free adapted CHOK1 derivative utilizing the glutamine synthetase (GS) gene expression system: positive transfectants were obtained under dual selection of methionine sulfoximine and glutamine-free media.

All these host cells or cell lines may be obtained from depositories such as the American Type Culture Collection (Manassas, Va., USA) or the Deutsche Sammlung von Mikroorganismen and Zellkulturen (Braunschweig, Germany) as well as from various commercial suppliers. Also within the present invention are primary mammalian cells, that is, cells directly obtained from an organism (at any developmental stage including inter alia blastocytes, embryos, larval stages, and adults). Examples of suitable primary cells comprise cardiomyocytes, primary hepatocytes, fibroblasts, neuronal cells, as well as stem cells. Also within the present invention are immortalized stable cell lines derived from primary cells.

In some embodiments, the host cell of the present invention constitutes a part of a multi-cellular organism. In other words, the invention also relates to transgenic mammalian organisms comprising at least one host cell as defined herein.

Within the present invention, the expression vector introduced may be propagated and maintained in the host cell as an independent genetic unit (i.e. episomally) (herein also referred to as "transient transfection") or vector fragments may become stably integrated into the host cell's genome (herein also referred to herein as "stable transfection"). Such recombination may either occur at random positions of the genome by non-homologous recombination or at specific positions of the genome by homologous recombination or via site-specific integrases. Preferably, the vector fragments (including the heterologous nucleic acid sequences to be expressed) become integrated in the host cell's genome as a single copy.

For introducing the expression vectors as defined herein into a mammalian host cell any transfection technique may be employed that is appropriate for the particular cell type employed. Numerous transfection methods are well established in the art including inter alia electroporation, calcium phosphate co-precipitation, chemical transfection (e.g., cyclodextrin, DEAE-dextran, polyethylenimine), lipofection, magnetofection, and "gene gun" (see, e.g., Sambrook, J., and Russel, D. W. (2001), supra; Ausubel, F. M. et al. (2001), supra).

In yet another aspect, the present invention relates to a method for heterologous expression of a nucleic acid sequence of interest in a mammalian host cell, comprising:
(i) transfecting the mammalian host cell with an expression vector as defined herein above; and
(ii) culturing the transfected mammalian host cell under conditions allowing the expression of the nucleic acid sequence of interest.

In other words, the present invention is also directed to a process for the recombinant (i.e. heterologous) production of polypeptides or proteins of interest in mammalian host cells being transfected with an expression vector as defined herein that comprise the corresponding nucleic acid sequences encoding said polypeptides or proteins. Transfection can be performed with a single expression vector or, as a co-transfection, with two or more different expression vectors.

As already outlined above, numerous methods are available for the transient or stable transfection of mammalian host cell. In preferred embodiments, the transfection is stable transfection in order to establish cells or cell lines the continuously express the heterologous nucleic acid sequences encoding the polypeptides or proteins of interest.

In some embodiments, the method further comprises the step of harvesting (and optionally purifying) the recombinant polypeptides or proteins produced. Depending on the nature of said polypeptides or protein they may become secreted into the cell culture supernatant, integrated in membrane of the host cell, or remain in an intracellular compartment.

Typically, if a unicellular mammalian host cell is employed the person skilled in the art can revert to a variety of cell culture conditions which allow the expression of the nucleic acid sequence of interest. Conveniently, the polypeptides or proteins produced are harvested (and optionally purified) from the culture medium, lysates or extracts of the cultured cells or from isolated (biological) membranes by established techniques, such as inter alia fractionated precipitation with salts or organic solvents, ion exchange chromatography, gel chromatography, size exclusion chromatography, HPLC, affinity chromatography (see, e.g., Sambrook, J., and Russel, D. W. (2001), supra). In case, the host cell is part of a multi-cellular organism, a fraction of these cells may serve as source for isolating the peptide of the invention.

Appropriate culture media and conditions for the above-described host cells are well known in the art (cf., e.g., Fresney, R. I. (2000) Culture of Animal cells. *A manual (4th Ed.)* Wiley-Liss, New York). Depending on the specific growth requirements of the host cell employed, mammalian cell culture can be performed, e.g., in RPMI 1640 medium, Ham's F12 medium or DMEM (Dulbecco's Modified Eagle Medium). Alternatively, a growth medium with a reduced serum concentration, such as OptiMEM, may be used. The media may optionally be supplemented with 10% (v/v) FCS (fetal calf serum), various growth factors, amino acids, antibiotics, and other additives Cell culture media specially adapted for CHO cells are described in, e.g., EP 0 481 791 81 and EP 1 525 320 81. The transfected mammalian host cells may be incubated at 37° C. in a 5% $CO_2$, water saturated atmosphere. The respective growth media, kits, and reagents are commercially available from various suppliers.

In a further aspect, the present invention relates to the use of an expression vector as defined herein above for the heterologous expression of a nucleic acid sequence of interest in a mammalian host cell. Preferably, the nucleic acid sequence of interest may encode a polypeptide or protein intended for diagnostic or therapeutic applications.

In preferred embodiments, the expression vector is used for the concomitant expression of two or more nucleic acid sequences of interest that are inserted into the expression vector under the control of separate chimeric promoter regulatory sequences. For example, an expression vector may be used for the expression of a gene of interest along with a reporter gene for monitoring cellular targeting and/or functionality of the gene of interest.

Particularly preferably, the expression vector is used for the concomitant expression of two or more nucleic acids sequences of interest that encode subunits of a dimeric or multimeric protein, for example, light and heavy chains of an antibody molecule or subunits of a vaccine. By employing different chimeric promoter regulatory sequences resulting in different gene expression rates an expression vector as defined herein may be used for the expression of two or more nucleic acid sequences of interest in a particular (molar) ratio.

In a specific embodiment, the expression vectors as defined herein are used as medicaments (or as parts of a medicament or kit-of-parts) for gene therapy.

The invention is further described by the figures and the following examples, which are solely for the purpose of illustrating specific embodiments of this invention, and are not to be construed as limiting the scope of the invention in any way.

EXAMPLES

Figure 3:
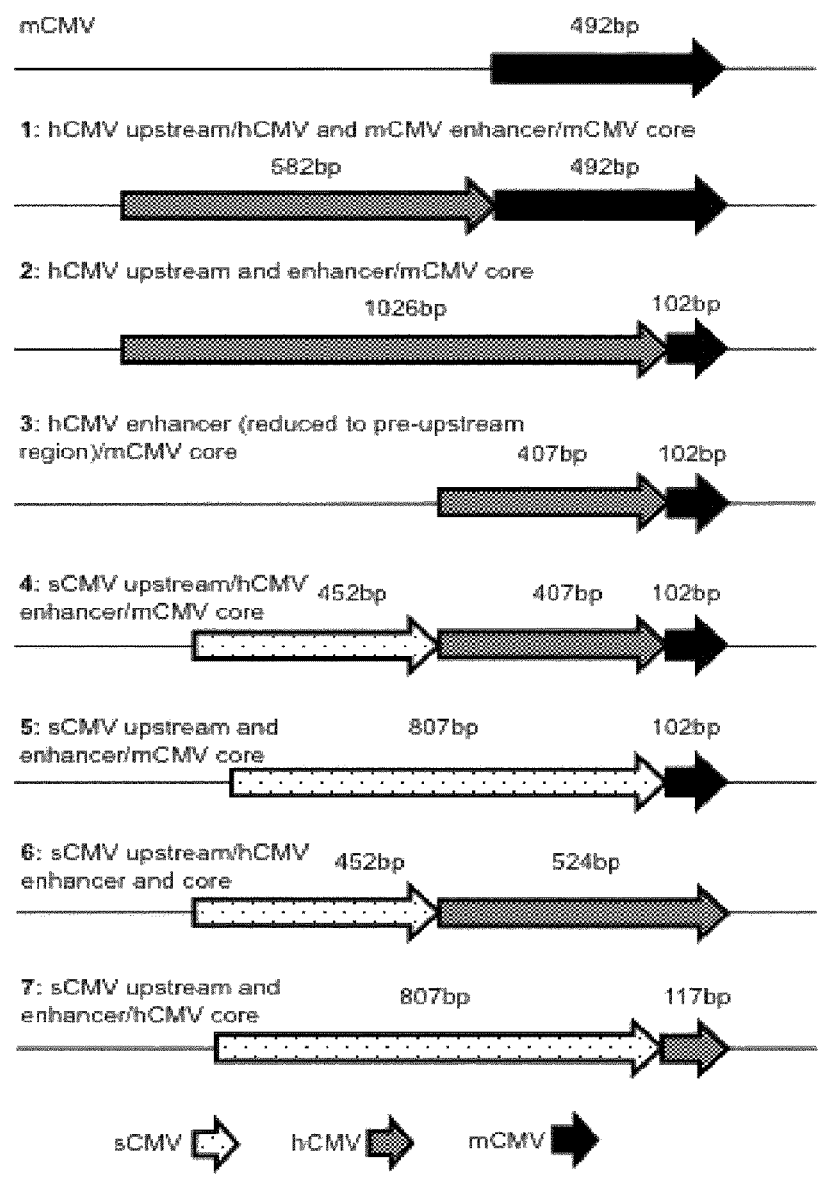
FIG. 3 schematically depicts the original mCMV promoter sequence (SEQ ID NO: 3) encompassed in pRY42 (top) as well as five different chimeric promoter regulatory sequences (constructs "1 to 5"), as defined herein (SEQ ID NO: 7 to SEQ ID NO: 11, respectively), which comprise murine CMV (mCMV) promoter sequences located 3' of upstream region and/or enhancer elements being derived from simian (sCMV) and/or human (hCMV) CMV. Furthermore, two additional chimeric promoter regulatory sequences (constructs "6 and 7"), as defined herein (SEQ ID NO: 12 and SEQ ID NO: 13) are shown, which comprise hCMV promoter sequences located 3' of upstream region and/or enhancer elements being derived from sCMV and/or human hCMV. All mCMV and hCMV promoter sequences specifically employed herein include at their 3'-ends an additional guanosine ("G") nucleotide, which represents the transcriptional start site.

Rationale:

Seven different chimeric promoter regulatory sequences, as specified in the claims, were generated based on sequences from the murine, human and simian cytomegalovirus (mCMV, hCMV, and sCMV) genomes (see Table 1, FIG. 3). These constructs were analyzed for their efficacy in controlling heterologous gene expression of the light and heavy chains (LC and HC) of a monoclonal antibody in Chinese hamster ovary (CHO) cells.

Example 1: Vector Construction

Gene synthesis was used to generate the seven different chimeric promoter regulatory constructs employed herein (i.e. constructs "1-7"). The constructs were provided ready for cloning into the "empty" targeting vector pRY42 (cf. FIG. 1, SEQ ID NO: 1), in order to replace the original murine cytomegalovirus (mCMV) promoters (SEQ ID NO: 3) contained therein. Parent vector pRY42 comprises two expression cassettes, each under the control of a promoter regulatory sequence (originally derived from mCMV).

The chimeric constructs (cf. Table 1, FIG. 3, SEQ ID NO: 7 to SEQ ID NO: 13) were synthesized to include additional DNA sequences at the 5' and 3' ends flanking the promoter regulatory sequences, thus allowing for the incorporation of endonuclease restriction sites (i.e. also present in pRY42) in order to facilitate exchange of nucleic acid fragments.

Table 1 illustrates the various sequence elements comprised in the chimeric promoter regulatory constructs 1-7 employed herein. Shown are the respective lengths and genetic locations of the individual regulatory sequences, as indicated in the NCBI Viral Genomes database (http://www.ncbi.nlm.nih.gov/genomes/GenomesHome; Bao, Y. et al. (2004) *J. Virol.* 78, 7291-7298). Notably, all mCMV or hCMV promoter sequences employed herein include at their 3'-end an additional guanosine ("G") nucleotide, which represents the transcriptional start site.

| Construct | sCMV length | NCBI viral genome accession no. | Coordinates | hCMV length | NCBI viral genome accession no. | Coordinates |
|---|---|---|---|---|---|---|
| 1 | — | — | — | 582 | X17403.1 | 174272-174873 |
| 2 | — | — | — | 1026 | X17403.1 | 173848-174873 |
| 3 | — | — | — | 407 | X17403.1 | 173848-174254 |
| 4 | 452 | U38308.1 | 3873-4324 | 407 | X17403.1 | 173848-174254 |
| 5 | 807 | U38308.1 | 3873-4679 | — | — | — |
| 6 | 452 | U38308.1 | 3873-4324 | 524 | X17403.1 | 173731-174254 |
| 7 | 807 | U38308.1 | 3873-4679 | 117 | X17403.1 | 173731-173847 |

| Construct | mCMV length | NCBI viral genome accession no. | Coordinates |
|---|---|---|---|
| 1 | 492 | U68299.1 | 182895-183386 |
| 2 | 102 | U68299.1 | 182895-182996 |
| 3 | 102 | U68299.1 | 182895-182996 |
| 4 | 102 | U68299.1 | 182895-182996 |
| 5 | 102 | U68299.1 | 182895-182996 |

The new vectors comprising chimeric constructs 1-7 were each constructed by a four way ligation reaction according to the scheme illustrated in Table 2. The chimeric promoter regulatory sequence for expression of the antibody light chain nucleic acid sequence was inserted 3' (i.e. "downstream") of the mutated FRT (Flippase Recognition Target) site (F5-mFRT) of pRY42, followed by an inter-chain fragment and the chimeric promoter regulatory sequence for expression of the antibody heavy chain nucleic acid sequence.

Ligation reactions were performed using the Rapid DNA Ligation Kit (Roche Diagnostics GmbH, Mannheim, Germany) according to the manufacturer's instructions. The resulting plasmid vectors were transformed int DH5α *E. coli* competent cells (Invitrogen/Life Technologies GmbH; Darmstadt, Germany). Samples were plated onto Luria-Bertani (LB) agar supplemented with 50 µg/ml ampicillin and incubated over-night at 37 CC. Single colonies were used to inoculate 500 ml shake flasks containing 200 ml LB liquid media plus 50 µg/ml ampicillin. Flasks were incubated over-night in a shaking incubator at 37° C., 200 rpm. Resultant cultures were used for preparation of plasmid DNA using a Nucleobond Maxi Kit (Macherey-Nagel GmbH, Duren, Germany) according to the manufacturer's instructions. Plasmids produced were verified by diagnostic restriction digest.

Table 2 shows the cloning scheme for generating chimeric promoter regulatory sequence constructs 1-5.

| Construct | LC regulatory element | Inter-chain fragment (derived from pRY42) | HC regulatory element | Vector backbone (derived from pRY42) |
|---|---|---|---|---|
| 1 | AatII-PacI | PacI-EcoRI | EcoRI-XhoI | XhoI-AatII |
| 2 | PvuI-SacII | SacII-EcoRI | EcoRI-Bsu36I | Bsu36I-PvuI |
| 3 | SspI-SacII | SacII-EcoRI | EcoRI-Bsu36I | Bsu36I-SspI |
| 4 | SspI-SacII | SacII-EcoRI | EcoRI-Bsu36I | Bsu36I-SspI |
| 5 | SspI-SacII | SacII-EcoRI | EcoRI-Bsu36I | Bsu36I-SspI |
| 6 | SspI-SacII | SacII-EcoRI | EcoRI-Bsu36I | Bsu36I-SspI |
| 7 | SspI-SacII | SacII-EcoRI | EcoRI-Bsu36I | Bsu36I-SspI |

Figure 2:
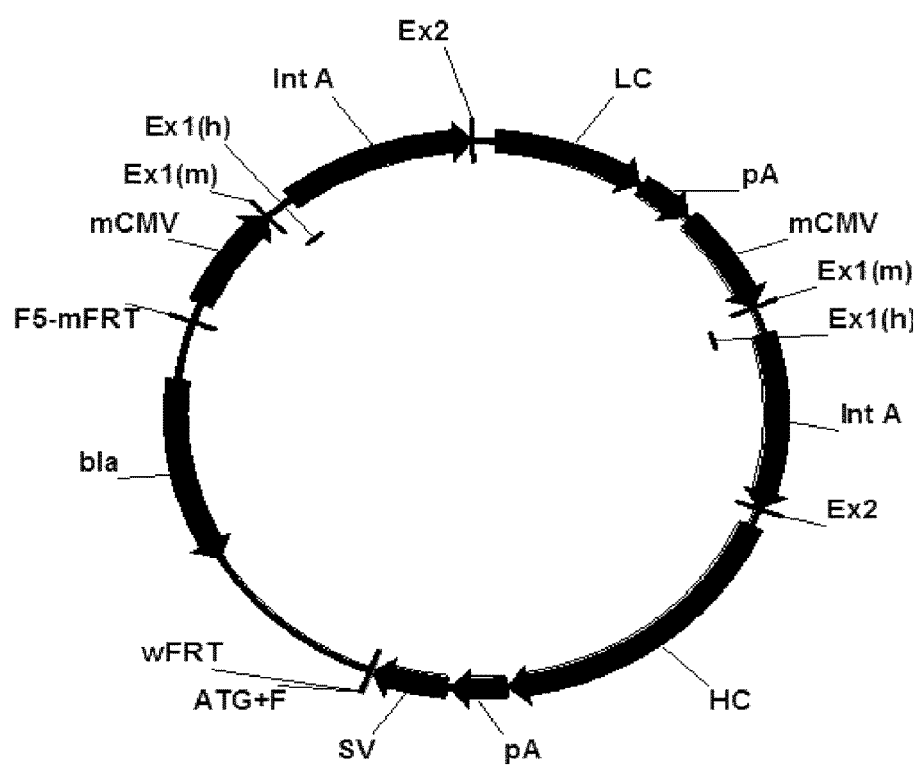
FIG. 2 illustrates expression vector pRY57 (SEQ ID NO: 2) encoding the light ("LC") and heavy ("HC") chains of the mouse-human chimeric monoclonal antibody (mAb) cB72.3 (Whittle, N. et al. (1987) *Protein Eng.* 1, 499-505), each located between the cloning sites 3' of the "Ex2" regions and the polyadenylation sites ("pA"), respectively. Otherwise, pRY57 is identical to pRY42. The LC and HC nucleic acid sequences of pRY57 were removed and cloned into pRY42 variants in which original the mCMV promoter sequence was replaced with the different chimeric promoter regulatory sequences as defined herein.

In a subsequent step, the LC and HC of IgG4 monoclonal antibody cB72.3 (Whittle, N. et al. (1987) *Protein Eng.* 1, 499-505) were cloned into each of the seven vectors comprising chimeric constructs 1-7. The nucleic acid sequences encoding the antibody chains were derived from vector pRY57 (FIG. 2, SEQ ID NO: 2) as EcoRI/HindIII (LC) and BamHI/NruI (HC) restriction fragments and cloned sequentially into the vectors for each promoter construct, using the same restriction endonucleases. Methods used were as described above. The resulting plasmid vectors were verified by diagnostic restriction digest and DNA sequencing of promoter regions, respectively.

Example 2: Transfection and Cell Line Construction

A cell line derived from suspension adapted Chinese hamster ovary cell line CHOK1SV was used for all experiments (Lonza Ltd., Basel, Switzerland). In this cell line, nucleic acid expression constructs are inserted at a specific genomic locus of the host cell and in defined copy number by means of a site-specific integration (SSI) system.

Positive selection for integration is accomplished by functional restoration of a hygromycin B resistance cassette present at the SSI site. Integration of the expression construct into the host genome also removes a copy of the thymidine kinase gene, which converts the pro-drug ganciclovir into a toxic, phosphorylated nucleotide analogue. Thus, addition of hygromycin B and ganciclovir during cell line construction provides positive and negative selection pressures, respectively, for integration at the target genomic locus.

The host cell line was revived from cryopreserved vials and sub-cultured. All cell culture was performed in CD-CHO medium (Invitrogen/Life Technologies GmbH; Darmstadt, Germany). 48 h prior to transfection, cells were seeded in 30 ml CD-CHO medium, at a final concentration of $0.3 \times 10^6$ cells/ml.

On the day of transfection, $1.2 \times 10^7$ cells were pelleted and re-suspended in 1 ml CD-CHO before co-transfection with 45 µg of pOG44 plasmid (Invitrogen/Life Technologies GmbH; Darmstadt, Germany) and 5 µg of each targeting vector (comprising chimeric constructs 1-7, respectively) was performed using electroporation in a 0.4 cm Bio-Rad GenePulser Xcell cuvette (single pulse 300 V I 900 µF, time constant 12-16 msec). The pOG44 plasmid encompasses an expression cassette for the yeast FLP recombinase (flippase) required to facilitate recombination at the FRT sites present at the target locus. All transfection experiments were performed at least in duplicate.

Each electroporation sample was transferred to 20 ml of CD-CHO medium in a T75 flask (BD Biosciences, Heidelberg, Germany) and incubated in static mode at 36.5° C., in a humidified incubator (5% (v/v) $CO_2$ in air). 48 h post-transfection cells were pelleted (150×g, 5 min) and re-suspended in 20 ml of CD-CHO medium containing 200 µg/ml hygromycin B (positive selection). The culture was maintained in static mode and after 72 h the medium exchanged with fresh CD-CHO containing 200 µg/ml hygromycin B.

Subsequently, every 72 h the viable cell concentration was determined and the medium exchanged with 20 ml fresh CD-CHO containing 200 µg/ml hygromycin B and 3 µM ganciclovir (negative selection). Once the culture in the T75 flask reached a total cell concentration of $9 \times 10^6$ cells/ml, the culture was adjusted to a final volume of 30 ml CD-CHO containing 200 µg/ml hygromycin B and 3 µM ganciclovir. Each diluted culture was then transferred to an E125 shake flask.

Example 3: Fed Batch Overgrow (FOG) Suspension Culture for Determining the Concentration of Monoclonal Antibody Produced by Using "Promoter Constructs 1-5"

Fed batch overgrow (FOG) shake flask analysis was performed as described in international patent publication WO 2008/148519 A2. All FOG experiments for a given transfected cell suspension culture were performed at least in duplicate.

In brief, transfected cells were seeded at a concentration of $2 \times 10^5$ cells/ml in 250 ml shake flasks, each containing 50 ml of CM42/SPE growth medium (Lonza Ltd., Basel, Switzerland) and incubated at 37° C. in a humidified orbital shaking incubator (5% (v/v) $CO_2$ in air) at 140 rpm. Cells were fed, starting on day 3 of the culture, with a feed consisting of mixture of amino acids and trace elements. Daily viabilities and viable cell concentrations were determined using a Cedex Automated Cell Viability Analyzer (Roche Diagnostics GmbH, Mannheim, Germany). Antibody concentration in the medium was determined by Protein A-HPLC on day 15 of culture (harvest of the "overgrown" cultures).

Example 4: Determination of the Concentration of Monoclonal Antibody Produced by Means of Protein A-HPLC (Using "Promoter Constructs 1-5")

The concentrations of the cB72.3 IgG4 monoclonal antibody (mAb) produced by the respective cell lines harboring the LC/HC gene expression cassettes under the control of the different chimeric constructs 1-5 and secreted to the cell culture medium were determined by Protein A-high performance liquid chromatography (HPLC). Cell-free supernatants (passed through a 0.22 µm filter unit) were loaded onto a POROS Protein A Immunodetection Column (applied Biosystems Inc., Foster City, Ca, USA), connected to an Agilent 1200 HPLC. The column was washed and bound mAb was eluted by lowering the pH of the solvent.

The concentration of the mAb was determined by comparison to a standard curve generated with serial dilutions of MabSelect SuRe-purified (GE Healthcare GmbH, Freiburg, Germany) cB72.3 IgG4 (range of standard curve: 1025 ng/µl to 200 ng/µl).

Figure 4:
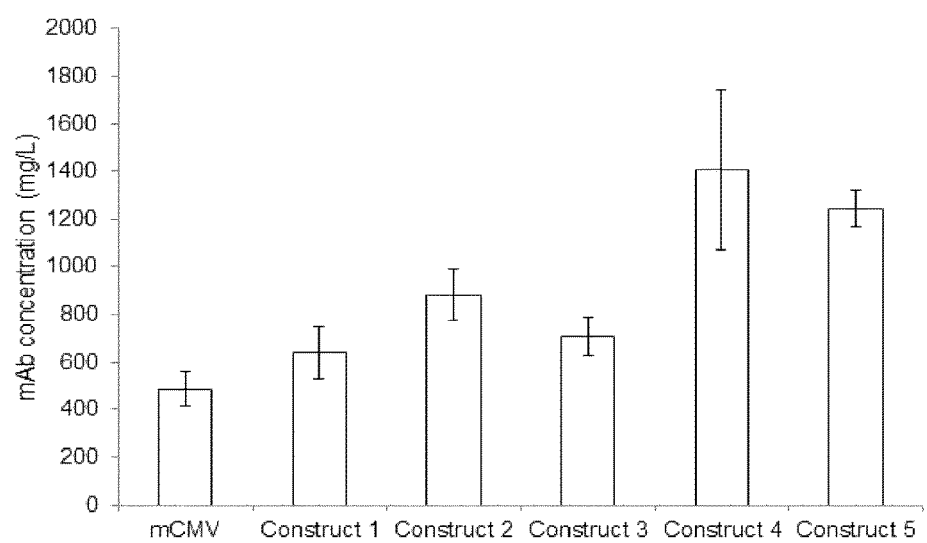
FIG. 4 shows a comparison of the concentrations of mAb cB72.3 produced in stable CHO lines where gene expression of the mAb sequences was under the control of chimeric constructs 1 to 5, as illustrated in FIG. 3. Determination was performed by Protein A HPLC after 15 days growth in 50 ml growth medium in E250 shake flask culture using a fed batch overgrow (FOG) protocol. For each of chimeric constructs, n=4, representing duplicate fed batch analyses for duplicate transfections, with the exception of construct 4, where n=6 (duplicate FOG analyses for triplicate transfections) and pRY57 (original mCMV), where n=8, with data points from experiments 1 and 2 being combined.

The results of the above experiments are summarized in Table 3 and FIG. 4, respectively: for each of chimeric constructs employed herein, n=4, representing duplicate FOG analyses for duplicate transfections, with the exception of construct 4, where n=6 (duplicate FOG analyses for triplicate transfections) and pRY57 (original mCMV), where n=8, with data points from experiments 1 and 2 being combined. The calculations of cell culture parameters were performed as described previously (Porter et al. (2010) *Biotechnol. Progr.* 26, 1446-1454).

From FIG. 4, it is evident that at the day of culture harvest (i.e. day 15), the use of any one of chimeric constructs no. 2-5 resulted in the production of higher antibody concentrations than with the use of the original mCMV promoter sequence (i.e. vector pRY57). The use of chimeric construct no. 1 also resulted in a higher antibody concentration than with the mCMV promoter (a factor of 1.31), even though the result does not reach statistical significance.

The best results were obtained with chimeric construct no. 4 resulting in an about 2.88 times higher gene expression as compared to the mCMV promoter, followed by (in descending order) chimeric construct no. 5 (factor of about 2.54), chimeric construct no. 2 (factor of about 1.80), and chimeric construct no. 3 (factor of about 1.45).

Table 3 illustrates the growth rates and the amounts of mAb produced by the different transfected host cell lines employed herein (comprising chimeric promoter regulatory sequences/constructs 1-5).

| | Transfectant pool/FOG | Max. ($10^6$ cells/ml) | µ (1/h) | IVC ($10^6$ cells · h/ml) | ρP | [mAb] (mg/l) |
|---|---|---|---|---|---|---|
| Experiment 1 | mCMV | 9.36 ± 1.02 | 0.0183 ± 0.0018 | 1523.35 ± 164.78 | 0.29 ± 0.02 | 439.74 ± 23.51 |
| | Construct 1 | 8.5 ± 0.75 | 0.0206 ± 0.0013 | 1445.11 ± 70.55 | 0.46 ± 0.07 | 638.87 ± 110.18 |
| | Construct 2 | 7.97 ± 0.41 | 0.0198 ± 0.0008 | 1409.29 ± 87.92 | 0.71 ± 0.06 | 883.10 ± 109.78 |
| | Construct 3 | 11.17 ± 1.02 | 0.0191 ± 0.0009 | 1873.58 ± 250.14 | 0.40 ± 0.03 | 707.98 ± 80.28 |
| Experiment 2 | mCMV | 9.29 ± 0.82 | 0.0143 ± 104.97 | 1790.34 ± 104.97 | 0.29 ± 0.05 | 539.31 ± 76.24 |
| | Construct 4 | 10.39 ± 0.90 | 0.0165 ± 0.0023 | 1848.05 ± 306.29 | 0.73 ± 0.22 | 1408.44 ± 337.47 |
| | Construct 5 | 11.58 ± 0.46 | 0.0139 ± 0.0028 | 2261.28 ± 50.84 | 0.46 ± 0.03 | 1244.15 ± 74.90 |

Legend: Max.—maximal viable cell concentration ($10^6$ cells/ml); µ—specific growth rate (1/h); IVG—time integral of viable cell concentration ($10^6$ cells · h/ml); ρP—specific production rate of the mAb (pg/cell · h); and [mAb]—concentration of the mAb produced at harvest (mg/l).

The above data show that the use of chimeric promoter regulatory sequences comprising sCMV and/or hCMV upstream region and/or enhancer elements in combination with mCMV promoter elements represent superior genetic tools for obtaining highly efficient heterologous gene expression systems for mammalian cells.

Example 5: Batch Overgrow (BOG) Suspension Culture for Determining the Concentration of Monoclonal Antibody Produced by Using "Promoter Constructs 6-7"

Batch cultures were performed in vented E125 flasks containing 30 ml CD-CHO in suspension mode (Kuhner 4 tier incubator, 36.5° C., 5% $CO_2$ in air (v/v) and 85% humidity (v/v)). In brief, transfected cells were seeded at a concentration of $2 \times 10^5$ cells/ml and viable cell concentrations were monitored throughout culture. Medium samples were taken at day seven of culture (high culture viability) for determination of the concentration of cB72.3 in medium using Protein A HPLC. All BOG experiments for a given transfected cell suspension culture were performed at least in duplicate.

Example 6: Determination of the Concentration of Monoclonal Antibody Produced by Means of Protein A-HPLC (Using "Promoter Constructs 6-7")

The concentrations of the cB72.3 IgG4 monoclonal antibody (mAb) produced by the respective cell lines harboring the LC/HG gene expression cassettes under the control of the different chimeric constructs 6-7 and secreted to the cell culture medium were determined by Protein A-high performance liquid chromatography (HPLC). Cell-free supernatants (passed through a 0.22 μm filter unit) were loaded onto a POROS Protein A Immunodetection Column (applied Biosystems Inc., Foster City, Ca, USA), connected to an Agilent 1100 HPLC. The column was washed and bound mAb was eluted by lowering the pH of the solvent.

The concentration of the mAb was determined by comparison to a standard curve generated with serial dilutions of MabSelect SuRe-purified (GE Healthcare GmbH, Freiburg, Germany) cB72.3 IgG4 (range of standard curve: 1025 ng/μl to 64 ng/μl).

Figure 5:
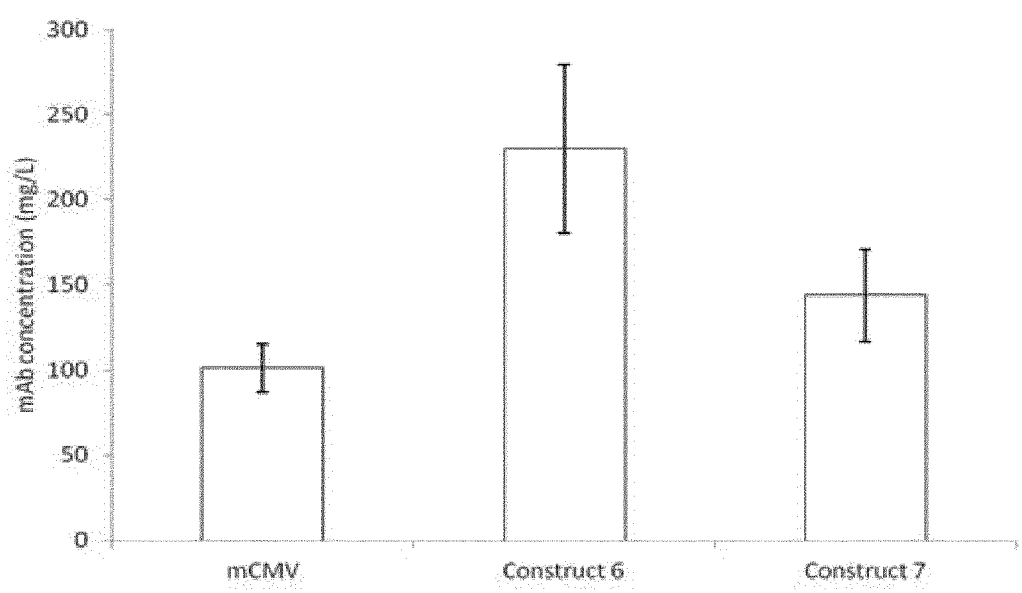
FIG. 5 shows a comparison of the concentrations of mAb cB72.3 produced in stable CHO lines where gene expression of the mAb sequences was under the control of chimeric constructs 6 and 7, as illustrated in FIG. 3. Determination was performed by Protein A HPLC after 7 days growth in 30 ml growth medium in E125 shake flask culture using a batch overgrow (BOG) protocol. For mCMV and construct 7, n=6 (duplicate batch analysis for triplicate transfections), and for construct 6, n=4 (duplicate batch analyses for duplicate transfections).

The results of the above experiments are summarized in FIG. 5: For mCMV and construct 7, n=6 (duplicate batch analysis for triplicate transfections), and for construct 6, n=4 (duplicate batch analysis for duplicate transfections).

From FIG. 5, it is evident that at day 7 of culture the use of any one of chimeric constructs 6 and 7 resulted in the production of higher antibody concentrations than with the use of the original mCMV promoter sequence (i.e. vector pRY57).

The best results were obtained with chimeric promoter construct 6 resulting in about 2.27 times higher mAb productivities as compared to the mCMV promoter.

The above data show that the use of chimeric promoter regulatory sequences comprising sCMV and/or hCMV upstream region and/or enhancer elements in combination with hCMV core promoter elements represent superior genetic tools for obtaining highly efficient heterologous gene expression systems for mammalian cells.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A mammalian host cell transfected with an expression vector, the vector comprising a first chimeric regulatory sequence being operably linked to a first nucleic acid sequence to be expressed, wherein the chimeric regulatory sequence comprises:
   (i) a promoter sequence from the murine or the human cytomegalovirus IE1 region and being operably linked to the transcriptional start site of the nucleic acid sequence to be expressed, wherein the promoter sequence is selected from the group consisting of SEQ ID NO: 4 and SEQ ID NO: 5; and
   (ii) an enhancer sequence from the simian cytomegalovirus IE1 region or representing a chimera from the human and simian cytomegalovirus IE1 regions, the enhancer sequence being located 5' of and operably linked to the murine or the human promoter sequence, wherein the enhancer sequence comprises SEQ ID NO: 6.

2. The mammalian host cell of claim 1, wherein the chimeric regulatory sequence of the expression vector comprises a nucleotide sequence being selected from the group consisting of SEQ ID NO: 8, SEQ ID NO: 9, SEQ ID NO: 10, SEQ ID NO: 11, SEQ ID NO: 12, and SEQ ID NO: 13.

3. The mammalian host cell of claim 1, wherein the host cell is a CHO cell.

4. The mammalian host cell of claim 1, wherein the expression vector further comprises a second chimeric regulatory sequence being operably linked to a second nucleic acid sequence to be expressed, wherein the second chimeric regulatory sequence is identical to the first chimeric regulatory sequence.

5. The mammalian host cell of claim 4, wherein the first and second nucleic acid sequences to be expressed encode different polypeptides.

6. The mammalian host cell of claim 5, wherein the different polypeptides represent subunits of a dimeric or multimeric protein.

7. The mammalian host cell of claim 6, wherein the dimeric or multimeric protein is an antibody molecule.

8. The mammalian host cell of claim 1, wherein the expression vector further comprises a second chimeric regulatory sequence being operably linked to a second nucleic acid sequence to be expressed, wherein the second chimeric regulatory sequence is different from the first chimeric promoter regulatory sequence.

9. The mammalian host cell of claim 8, wherein the first and second nucleic acid sequences to be expressed encode different polypeptides.

10. The mammalian host cell of claim 9, wherein the different polypeptides represent subunits of a dimeric or multimeric protein.

11. The mammalian host cell of claim 10, wherein the dimeric or multimeric protein is an antibody molecule.

12. A method for heterologous expression of a nucleic acid sequence of interest in a mammalian host cell, comprising:
(i) transfecting the mammalian host cell with an expression vector, the vector comprising a first chimeric regulatory sequence being operably linked to a first nucleic acid sequence to be expressed, wherein the chimeric regulatory sequence comprises:
(xi) a promoter sequence from the murine or the human cytomegalovirus IE1 region and being operably linked to the transcriptional start site of the nucleic acid sequence to be expressed, wherein the promoter sequence is selected from the group consisting of SEQ ID NO: 4 and SEQ ID NO: 5; and
(xii) an enhancer sequence from the simian cytomegalovirus IE1 region or representing a chimera from the human and simian cytomegalovirus IE1 regions, the enhancer sequence being located 5' of and operably linked to the murine or the human promoter sequence, wherein the enhancer sequence comprises SEQ ID NO: 6; and
(ii) culturing the transfected mammalian host cell under conditions allowing the expression of the nucleic acid sequence of interest.

13. The method of claim 12, wherein the chimeric promoter regulatory sequence of the expression vector comprises a nucleotide sequence being selected from the group consisting of SEQ ID NO: 8, SEQ ID NO: 9, SEQ ID NO: 10, SEQ ID NO: 11, SEQ ID NO: 12, and SEQ ID NO: 13.

14. The method of claim 12, wherein the transfection is stable transfection.

* * * * *